(12) United States Patent
Gorfinkel et al.

(10) Patent No.: US 8,828,209 B2
(45) Date of Patent: Sep. 9, 2014

(54) MASSIVELY PARALLEL 2-DIMENSIONAL CAPILLARY ELECTROPHORESIS

(75) Inventors: Vera Gorfinkel, Stony Brook, NY (US); Evgeni A. Kabotyanski, Stony Brook, NY (US); Boris Gorbovitski, Port Jefferson Station, NY (US)

(73) Assignee: The Research Foundation for the State University of New York, Albany, NY (US)

(*) Notice: Subject to any disclaimer, the term of this patent is extended or adjusted under 35 U.S.C. 154(b) by 1979 days.

(21) Appl. No.: 11/922,515

(22) PCT Filed: Jun. 22, 2006
(Under 37 CFR 1.47)

(86) PCT No.: PCT/US2006/024626
§ 371 (c)(1),
(2), (4) Date: Jul. 28, 2011

(87) PCT Pub. No.: WO2007/002490
PCT Pub. Date: Jan. 4, 2007

(65) Prior Publication Data
US 2012/0152742 A1      Jun. 21, 2012

Related U.S. Application Data

(60) Provisional application No. 60/692,564, filed on Jun. 22, 2005.

(51) Int. Cl.
*G01N 27/447* (2006.01)
*G01N 27/453* (2006.01)
(52) U.S. Cl.
USPC ............ 204/453; 204/604; 204/601; 204/451
(58) Field of Classification Search
USPC ................. 204/601, 604, 605, 451, 453, 455
See application file for complete search history.

(56) References Cited

U.S. PATENT DOCUMENTS

| | | | |
|---|---|---|---|
| 5,120,414 A | * | 6/1992 | Carson et al. ............... 204/453 |
| 5,784,157 A | | 7/1998 | Gorfinkel et al. ............ 356/318 |
| 6,464,852 B1 | | 10/2002 | Gorfinkel et al. ............ 204/600 |

(Continued)

OTHER PUBLICATIONS

Alaverdian, et al., "A family of novel DNA sequencing instruments based on single-photon detection." *Electrophoresis*, 23(16):2804-2817 (2002).

(Continued)

*Primary Examiner* — Alex Noguerola
(74) *Attorney, Agent, or Firm* — Medlen & Carroll, LLP

(57) ABSTRACT

This invention discloses a highly efficient method, system and apparatus for nucleic acid analysis, including sequencing (both automated re-sequencing and de-novo sequencing). The system is capable of sequencing DNA sizes ranging from fragments to mammalian size genomes having mouse draft quality at a much reduced cost. The system comprises a massive parallel capillary electrophoretic separation using two-dimensional monolith multi-capillary arrays (2D-MMCA). Sequence identification can be performed using fluorescent or otherwise labeled dideoxynucleotide-terminated DNA extension product generated by gel matrix-, or beads-, or substrate tethered-, or otherwise immobilized colonies of single template molecules. Cost reduction is a significant advantage over currently known methods because of: (i) using massively parallel sub-nanoliter volume reactions; and (ii) employing 2D-MMCAs that increase the throughput of the CE separation and detection by at least two orders of magnitude compared to the commercial high-throughput DNA machines.

33 Claims, 29 Drawing Sheets

(56) References Cited

U.S. PATENT DOCUMENTS

| | | | |
|---|---|---|---|
| 6,660,149 B1* | 12/2003 | Karger et al. | 204/601 |
| 6,707,548 B2 | 3/2004 | Kreimer et al. | 356/301 |
| 6,740,219 B2 | 5/2004 | Imai et al. | 204/603 |
| 6,794,127 B1 | 9/2004 | Lafferty et al. | 435/4 |

OTHER PUBLICATIONS

Bilenko, et al., "Formation of a resistive region at the anode end in DNA capillary electrophoresis." *Electrophoresis*, 24(7-8):1176-1183 (2003).
Blanchard, et al., "High-density oligonucleotide arrays." *Biosensors and Bioelectronics*, 11(6-7):687-690 (1996).
Braslavsky, et al., "Sequence information can be obtained from single DNA molecules." *PNAS USA*, 100(7):3960-3964 (2003).
Brenner, et al., "Gene expression analysis by massively parallel signature sequencing (MPSS) on microbead arrays." *Nat Biotechnol*, 18(6):630-634 (2000).
Chetverina and Chetverin, "Cloning of RNA molecules in vitro." *Nucleic Acids Res*, 21(10):2349-2353 (1993).
Chetverina, et al., "Molecular colony diagnostics: detection and quantitation of viral nucleic acids by in-gel PCR." *Biotechniques*, 33(1):150-152, 154, 156 (2002).
Deamer and Akeson, "Nanopores and nucleic acids: prospects for ultrarapid sequencing." *Trends Biotechnol*, 18(4):147-151 (2000).
DiCesare, et al., "A High-Sensitivity Electrochemiluminescence-Based Detection System for Automated PCR Product Quantitation." *Biotechniques*, 15(1):152-157 (1993).
Dressman, et al., "Transforming single DNA molecules into fluorescent magnetic particles for detection and enumeration of genetic variations." *PNAS USA*,100(15):8817-8822 (2003).
Drmanac, et al., "Accurate sequencing by hybridization for DNA diagnostics and individual genomics." *Nat Biotechnol*, 16(1):54-58 (1998).
Emrich, et al., "Microfabricated 384-lane capillary array electrophoresis bioanalyzer for ultrahigh-throughput genetic analysis." *Anal Chem*, 74(19):5076-5083 (2002).
Gavrilov, et al., "Dynamic range of fluorescence detection and base-calling accuracy in DNA sequencer based on single-photon counting." *Electrophoresis*, 24(7-8):1184-1192 (2003).
Gillespie and Spiegelman, "A quantitative assay for DNA-RNA hybrids with DNA immobilized on a membrane." *J Mol Biol*, 12(3):829-842 (1965).
Hashimoto, et al., "On-line integration of PCR and cycle sequencing in capillaries: from human genomic DNA directly to called bases." *Nucleic Acids Res*, 31(8):e41 (2003).
Heller, "Influence of electric field strength and capillary dimensions on the separation of DNA." *Electrophoresis*, 21(3):593-602 (2000).
Hughes, et al., "Expression profiling using microarrays fabricated by an ink-jet oligonucleotide synthesizer." *Nat Biotechnol*, 19(4):342-347 (2001).
Kafatos, et al., "Dot hybridization and hybrid-selected translation: methods for determining nucleic acid concentrations and sequence homologies." *Gene Amplif Anal*, 2:537-550 (1981).
Kartalov and Quake, "Microfluidic device reads up to four consecutive base pairs in DNA sequencing-by-synthesis." *Nucleic Acids Res*, 32(9):2873-2879 (2004).
Khrapko, et al., "An oligonucleotide hybridization approach to DNA sequencing." *FEBS Lett*, 256(1-2):118-122 (1989).
Korlach, "A new strategy for sequencing individual molecules of DNA." *Biophysical Journal*, 80:147A (2001).
Koutny, et al., "Eight hundred-base sequencing in a microfabricated electrophoretic device." *Anal Chem*, 72(14):3388-3391 (2000).
Lagally, et al., "Single-molecule DNA amplification and analysis in an integrated microfluidic device." *Anal Chem*, 73(3):565-570 (2001).
Lage, et al., "Whole genome analysis of genetic alterations in small DNA samples using hyperbranched strand displacement amplification and array-CGH." *Genome Res*, 13(2):294-307 (2003).
Leamon, et al., "A massively parallel PicoTiterPlate based platform for discrete picoliter-scale polymerase chain reactions." *Electrophoresis*, 24(21):3769-3777 (2003).
Levene, et al., "Zero-Mode Waveguides for Single-Molecule Analysis at High Concentrations." *Science*, 299(5607):682-686 (2003).
Lipshutz, et al., "Using oligonucleotide probe arrays to access genetic diversity." *Biotechniques*, 19(3):442-447 (1995).
Lizardi, et al., "Mutation detection and single-molecule counting using isothermal rolling-circle amplification." *Nat Genet*, 19(3):225-232 (1998).
Margraf, et al., "Single-Tube Method for Nucleic Acid Extraction, Amplification, Purification, and Sequencing." *Clinical Chemistry*, 50(10):1755-1761 (2004).
Maskos and Southern, "A novel method for the analysis of multiple sequence variants by hybridisation to oligonucleotides." *Nucleic Acids Research*, 21(9):2267-2268 (1993).
Meller, et al., "Ordered assembly of *roX* RNAs into MSL complexes on the dosage-compensated X chromosome in *Drosophila*." *Current Biology*, 10(3):136-143 (2000).
Mitra and Church, "In situ localized amplification and contact replication of many individual DNA molecules." *Nucleic Acids Res*, 27(24):e34 (1999).
Mitra, et al., "Fluorescent in situ sequencing on polymerase colonies." *Anal Biochem*, 320(1):55-65 (2003).
Nagai, et al., "High Throughput Single Cell PCR on a Silicon Microchamber Array." in *Micro Total Analysis Systems 2001* (Ramsey, et al., Eds.), pp. 268-270, Springer Netherlands (2001).
Paegel, et al., "Microfluidic devices for DNA sequencing: sample preparation and electrophoretic analysis." *Curr Opin Biotechnol*, 14(1):42-50 (2003).
Patil, et al., "Blocks of Limited Haplotype Diversity Revealed by High-Resolution Scanning of Human Chromosome 21." *Science*, 294(5547):1719-1723 (2001).
Pourmand, et al., "Multiplex Pyrosequencing." *Nucleic Acids Res*, 30(7):e31 (2002).
Ronaghi, et al., "Real-time DNA sequencing using detection of pyrophosphate release." *Anal Biochem*, 242(1):84-89 (1996).
Ronaghi, "Pyrosequencing Sheds Light on DNA Sequencing." *Genome Research*, 11(1):3-11 (2001).
Rubina, et al., "Hydrogel drop microchips with immobilized DNA: properties and methods for large-scale production." *Anal Biochem*, 325(1):92-106 (2004).
Sanger, et al., "DNA sequencing with chain-terminating inhibitors." *PNAS USA*, 74(12):5463-5467 (1977).
Shendure, et al., "Advanced Sequencing Technologies: Methods and Goals." *Nat Rev Genet*, 5(5):335-344 (2004).
Singer, et al., "Libraries for Genomic SELEX." *Nucleic Acids Res*, 25(4):781-786 (1997).
Soper, et al., "Sanger DNA-sequencing reactions performed in a solid-phase nanoreactor directly coupled to capillary gel electrophoresis." *Anal Chem*, 70(19):4036-4043 (1998).
Southern, et al., "Molecular interactions on microarrays." *Nat Genet*, 21(1 Suppl):5-9 (1999).
Strizhkov, et al., "PCR Amplification on a Microarray of Gel-Immobilized Oligonucleotides: Detection of Bacterial Toxin- and Drug-Resistant Genes and Their Mutations." *Biotechniques*, 29(4):844-848, 850-852, 854 passim—A pp. 844-848, 850-852 (2000).
Strizhkov, et al., "PCR Amplification on a Microarray of Gel-Immobilized Oligonucleotides: Detection of Bacterial Toxin- and Drug-Resistant Genes and Their Mutations." *Biotechniques*, 29(4):844-848, 850-852, 854 passim—B pp. 854 passim (2000).
Tillib and Mirzabekov, "Advances in the analysis of DNA sequence variations using oligonucleotide microchip technology." *Curr Opin Biotechnol*, 12(1):53-58 (2001a).
Tillib, et al., "Integration of multiple PCR amplifications and DNA mutation analyses by using oligonucleotide microchip." *Anal Biochem*, 292(1):155-160 (2001b).
van den Boom, et al., "Forward and reverse DNA sequencing in a single reaction." *Anal Biochem*, 256(1):127-129 (1998).

(56) References Cited

OTHER PUBLICATIONS

Vasiliskov, et al., "Fabrication of microarray of gel-immobilized compounds on a chip by copolymerization." *Biotechniques*, 27(3):592-594, 596-598, 600 passim (1999).

Walker, et al., "Isothermal in vitro amplification of DNA by a restriction enzyme/DNA polymerase system." *PNAS USA*, 89(1):392-396 (1992).

Waterston, et al., "Initial sequencing and comparative analysis of the mouse genome." *Nature*, 420(6915):520-562—A pp. 520-539 (2002).

Waterston, et al., "Initial sequencing and comparative analysis of the mouse genome." *Nature*, 420(6915):520-562—B pp. 540-562 (2002).

Werle, et al., "Convenient single-step, one tube purification of PCR products for direct sequencing." *Nucleic Acids Res*, 22(20):4354-4355 (1994).

Westin, et al., "Anchored multiplex amplification on a microelectronic chip array." *Nat Biotechnol*, 18(2):199-204 (2000).

Winters-Hilt, et al., "Highly Accurate Classification of Watson-Crick Basepairs on Termini of Single DNA Molecules." *Biophysical journal*, 84(2):967-976 (2003).

ISR PCT/US2006/024626 Mailed Jul. 3 (2006).

Michels, et al., "Fully Automated Two-dimensional Capillary Electrophoresis for High Sensitivity Protein Analysis." *Molecular and Cellular Proteomics*, 1: 69-74 (2002).

\* cited by examiner

Panel A

Panel B

MASSIVELY PARALLEL 2-DIMENSIONAL CAPILLARY ELECTROPHORESIS

FIELD OF INVENTION

The present invention relates to nucleic acid analysis and to nucleotide sequencing in particular. In one embodiment, the sequencing is performed using capillary electrophoresis. In one embodiment, the capillaries are arranged in a fused array. In one embodiment, the fused capillary array is loaded with sequencing product using electrokinetic technology. In one embodiment, sequencing product is made in isolated, addressable spots.

BACKGROUND OF THE INVENTION

The goal to elucidate the entire human genome has created an interest in technologies for rapid DNA sequencing, both for small and large-scale applications. Sequencing speed, length of sequence that can be read during a single sequencing run, and amount of nucleic acid template required are all proper considerations to improve sequencing methods.

These research challenges suggest aiming to sequence the genetic information of single cells without the need for time-consuming, one-at-a-time, analysis techniques. Large-scale genome projects are currently too expensive to realistically be carried out for a large number of organisms or patients. Furthermore, as knowledge of the genetic basis for human diseases increases, there will be an ever-increasing need for accurate, high-throughput DNA sequencing that is affordable for clinical applications. Practical methods for determining the base pair sequences of single molecules of nucleic acids, preferably with high speed and long read lengths, would provide the necessary measurement capability.

What is needed is a highly automated, cost effective, and highly parallel system that can simultaneously sequence thousands of nucleotide fragments.

SUMMARY

The present invention relates to nucleic acid analysis, including nucleic acid sequencing. In one embodiment, the sequencing is performed using capillary electrophoresis. In one embodiment, the capillaries are arranged in a fused array. In one embodiment, the fused capillary array is loaded with sequencing product using electrokinetic technology.

In one aspect, the invention is a system for analyzing nucleic acids comprising a plurality of nucleic acid-immobilizing pads disposed on a solid substrate having an electrically conductive element; the system further comprises a plurality of capillaries arranged, preferably, in a regular two-dimensional array, each capillary alignable at one end with a nucleic acid-immobilizing pad that does not contact the pad, alignable at the other end with a photodetector in an array of photodetectors configured to detect a nucleic acid marker in the capillary. The system includes a buffer reservoir wherein each capillary is in fluid communication with the reservoir. The pads of the system can be subjected to an electrical bias that urges nucleic acids from the pad into the capillary tube wherein the nucleic acids are electrophoresed. The system provides a source of illumination, preferably a laser that side-illuminates several capillaries at once as the beam scans the array row-by-row. The illumination excites fluorophores that mark the nucleic acids in the tube and the fluorophores emit light collected by the photodetectors. Finally, the system provides a means of processing the data acquired by the photodetectors to convert the data into nucleic acid sequence information.

In a preferred embodiment, the present invention contemplates a system for nucleic acid analysis comprising a) a plurality of pads disposed on a solid substrate, at least a portion of said pads comprising nucleic acid, at least a portion of said nucleic acid comprising a marker, said substrate comprising an electrically conductive element; b) a plurality of capillaries, each said capillary comprising first and second ends, said first end alignable with a pad in said plurality of pads without contacting said pad, said second end alignable with c) a photodetector (or plurality of photodetectors) configured to detect said marker when said nucleic acid is in said capillaries. Each pad has a defined area and is spaced away from another pad. Each pad may be semi-solid (e.g. comprising gel, foam, etc.). In a preferred embodiment, there is no direct contact between the pads and the capillaries.

The present invention contemplates an array of pads (e.g. gel pads) on a substrate, said substrate comprising an electrically conductive element. Such an array can be sold as a standalone element and/or as part of a kit. Such pads may be manipulated by the end user to contain bioreagents (e.g. primers, PCR amplification reagents, etc.) in customized reactions.

In a preferred embodiment, the above-described system further comprises d) a buffer reservoir, wherein each said capillary is in fluid communication with said reservoir; e) a means of electrically biasing at least a portion of said plurality of capillaries with respect to said electrically conductive element such that an electric current passes through said pad and said capillary to said reservoir, f) an illumination source capable of side-illuminating at least a portion of said plurality of capillaries near said second end of each capillary in said portion such that said marker emits a photon detectable by said photodetector, and g) a means for processing data acquired by said plurality of photodetectors. It is preferred that said photodetector faces said second end of said capillary. It is preferred said buffer reservoir is transparent and is interposed between said photodetector and said capillary.

It is not intended that the present invention be limited by the configuration of the pads or configuration of the capillaries. In one embodiment, said plurality of pads are configured as a two-dimensional array. In one embodiment, said plurality of capillaries is cross-sectionally a two-dimensional array. In a preferred embodiment, said plurality of capillaries is a monolith.

The present invention contemplates, in some embodiments, that other elements are part of the system. For example, in one embodiment, the system further comprises a diffusion barrier surrounding each said pad. In another embodiment, the system further comprises a removable dam that is capable of retaining liquid on a specified region of said pad array. In still another embodiment, the system further comprises a dam top cover.

A variety of designs is possible for the substrate and conductive elements. For example, in one embodiment, said electrically conductive element is discontinuous such that each said pad is electrically isolated from all other said pads. In one embodiment, at least one said pad is in electrical contact with at least one other said pad.

It is not intended that the present invention be limited by the manner in which the pads are arrayed. In one embodiment, the system further comprising a spotting machine, wherein said spotting machine is capable of spotting said array of pads in register with said capillary array. These pads may be spotted with bioreagents (e.g. nucleic acid) or without bioreagents (e.g. only buffer or other solutions). In the case where a limiting dilution approach is used for bioreagents, some pads will (statistically) contain nucleic acid while others will not. In one embodiment, said spotting machine is capable of spotting said nucleic acid-immobilizing pads comprising a primer covalently attached thereto. In another embodiment, said spotting machine is capable of spotting said nucleic acid-immobilizing pads comprising template DNA. In yet another embodiment, said spotting machine is capable of spotting said nucleic acid-immobilizing pads comprising DNA amplification reactants.

It is not intended that the present invention be limited to a particular light source. In one embodiment, aid illumination source is a laser configured to emit a beam capable of entering said capillary array normal to a sidewall of said capillary array and exiting said capillary array normal to a wall opposite said sidewall. In one embodiment, said laser beam scans said capillary array. In another embodiment, said laser beam traverses an optical line generator before entering said capillary array. In still another embodiment, said laser beam comprises mutually focused, temporally modulated beams.

It is also not intended that the present invention be limited to a particular type of photodetector. In one embodiment, said photodetector is a single photon detector (capable of detecting single photons).

It is not intended that the present invention be limited by the nature of the marker(s) employed. In one embodiment, markers which have detectable electromagnetic spectral properties are employed. In one embodiment, markers which are highly fluorescent when excited with UV (ultraviolet) radiation are employed (e.g. dyes, fluorophores, etc.). In one embodiment, markers comprising one or more physical properties that facilitate detection are employed. Useful physical properties include a characteristic electromagnetic spectral property such as emission or absorbance, magnetism, electron spin resonance, electrical capacitance, dielectric constant or electrical conductivity. Markers may be ferromagnetic, paramagnetic, diamagnetic, luminescent, electrochemiluminescent, fluorescent, phosphorescent, chromatic or have a distinctive mass. Fluorescent moieties which are useful as markers include (but are not limited to) dansyl fluorophores, coumarins and coumarin derivatives, fluorescent acridinium moieties and benzopyrene based fluorophores. Preferably, the fluorescent marker has a high quantum yield and can be excited in both the UV and visible portion of the spectrum. Upon excitation at a preselected wavelength, the marker is detectable at low concentrations either visually or using conventional fluorescence detection methods. Electrochemiluminescent markers such as ruthenium chelates and its derivatives or nitroxide amino acids and their derivatives are preferred when extreme sensitivity is desired (J. DiCesare et al., BioTechniques 15:152-59, 1993). These markers are detectable at the femtomolar ranges and below.

In addition to fluorescent markers, a variety of markers possessing other specific physical properties can be used. In general, these properties are based on the interaction and response of the marker to electromagnetic fields and radiation and include absorption in the UV, visible and infrared regions of the electromagnetic spectrum, presence of chromophores which are Raman active, and can be further enhanced by resonance Raman spectroscopy, electron spin resonance activity and nuclear magnetic resonances and use of a mass spectrometer to detect presence of a marker with a specific molecular mass.

It is not intended that the present invention be limited by the manner in which the nucleic acid and marker interact. In one embodiment, the marker is covalently attached to the nucleic acid. In another embodiment, the marker is non-covalently attached. In another embodiment, the marker is attached to a nucleic acid precursor (e.g. dNTP, ddNTP, etc.) and incorporated into a nucleic acid extension product.

It is not intended that the present invention be limited by the manner in which the marker is excited or detected. In one embodiment, said laser beam excites an emission of light from a fluorophore traversing said capillary, said emission collected as said emission exits said first end of said capillary. In one embodiment, a fiber optic device collects said emission. In one embodiment, said fiber optic device and said laser beam scan said monolith in synchrony. In one embodiment, an array of said photodetectors is employed and they are capable, of detecting colors.

It is not intended that the present invention be limited by the number of capillaries (or capillary tubes) in the system. In one embodiment, said capillary array is more than 8 capillaries to less than 400 capillaries in a first direction and more than 8 capillaries to less than 400 capillaries in a second direction orthogonal to said first direction. In a preferred embodiment, said capillary array is more than 700 capillaries and less than 1000.

It is not intended that the present invention be limited by the precise dimensions of the capillaries. In one embodiment, said capillary has a thickness of more than about 30 micrometers and less than about 100 micrometers. In one embodiment, said capillary has a bore of more than about 900 square micrometers and less than about 2500 square micrometers. In one embodiment, said capillary has a length of more than about 5 cm and less than about 20 cm.

It is not intended that the present invention be limited to the material used to make the capillaries. In one embodiment, said capillary comprises fused silica.

It is not intended that the present invention be limited by the precise dimensions of the pads. In one embodiment, said pad has a water holding capacity of more than about 100 picoliters.

In another aspect, the invention is a method of analyzing nucleic acids in a massively parallel manner. In one embodiment, the present invention contemplates a method of nucleic acid analysis, comprising: a) providing the system as described above; b) aligning said plurality of capillaries with said plurality of pads without contacting said pads with said capillaries; and c) causing an electric current to pass through at least a portion of said pads and at least a portion of said capillaries to said reservoir by said means of electrically biasing at least a portion of said plurality of capillaries with respect to said electrically conductive element such that at least a portion of said nucleic acid enters said first ends of at least a portion of said capillaries. In one embodiment, the method further comprises: a) aligning said photodetector (or plurality of photodetectors) with said second ends of said plurality of capillaries; and b) detecting nucleic acid in at least a portion of said capillaries by detecting said marker. In one embodiment, said marker emits a photon upon excitation with said illumination source. In one embodiment, said marker is selected from the group consisting of dyes and fluorophores. In one embodiment, said pads comprise gel pads. Using the above-described method, it is possible to utilize the system to determine one or more properties of the nucleic acid, such as the composition, partial sequence or complete sequence.

Variations on the above-described system design and method(s) are contemplated. In one embodiment, the present invention contemplates constructing (and using) a pair of solid supports (e.g. a pair of plates). In one embodiment, the present invention contemplates A method of determining the nucleotide sequence of a DNA sample comprising: a) providing: i) a pair of mirror-symmetrical plates, comprising a first plate and a second plate, wherein said first plate comprises a surface contacted with a PCR reaction mixture having a first primer and said a second plate comprises a surface contacted with a PCR reaction mixture having a second primer, and ii) a solution of DNA template; b) spotting said solution of DNA template onto said first plate; c) covering said spotted first plate with said second plate, thereby, creating a plate complex. In a preferred embodiment, a portion of said DNA spotted on said first plate is transferred to said second plate. In a further embodiment, the method comprises d) reacting said plate complex with dye containing reagents under conditions such that said spotted templates on said first and second plates are amplified and labeled; e) resolving the nucleic acids within said amplified and labeled spotted templates on said first and said second plate; and f) detecting said resolved nucleic acids, of step e), under conditions such that the nucleotide sequence of said DNA sample is determined.

DEFINITIONS

The term "in register" or "registerable" refers to the invention's ability to back-track from the readout of a detector to the initial samples to be analyzed even when 300,000 or more such samples are processed in a single cycle of the apparatus. Thus, capillaries are said to be registerable because the system is capable of aligning each capillary in an array with a detector (e.g., a photodetector) addressed to that capillary. The alignment is sufficiently precise to permit the detector to pick up an adequate fraction of the signal (e.g., an emission of fluorescent light) to be detected without uncontrollable "cross-talk" from neighboring capillaries. At the same time, the system aligns each capillary with a sample immobilized in a spot of gel addressed to that capillary. Alignment is precise enough to allow an adequate fraction of the sample to be electrokinetically ejected from the gel spot into the capillary—without any direct contact between gel and capillary.

The term "pad" herein refers generally to any spot of material deposited on a supporting substrate and sized and positioned in such a way that it can be aligned with a specified capillary, including a capillary in the two-dimensional capillary array of the invention. Although a pad is typically a gel material, any material that can be deposited on a supporting substrate without spreading substantially from the site where it was deposited is within the scope of the definition, as long as the material is compatible with the processes of the invention. The "pad" may contain template DNA or RNA, and reactants and products of an amplification reaction such as but not limited to PCR, or reactants and products of a nucleic acid sequencing process. By way of example and not of limitation, a pad may simply be a site within a slab of gel that absorbs a deposited droplet of a solution, or the pad may be deposited thick enough to project substantially above the plane of its supporting substrate. The pad can absorb template DNA or RNA, PCR reactants and enzymes, and Sanger sequencing reactants and enzymes by in-diffusion from solution. Pads may also referred to herein as "gel pads," "spots," or "polonies." Preferred gel pads "immobilize" nucleic acids and the reactants and products of the invention. Immobilization is not to be confused with preventing diffusion. In fact, the ideal gel pad of the invention absorbs nucleic acids, etc. readily and these molecules diffuse within the pad readily. They are immobilized because means are provided to keep the molecules from diffusing out of the pad readily and because the pads themselves tend not to migrate.

An "electrically conductive element" is a layer of electrically conductive material, which can be a metal or metal alloy ($In_2O_3$ is exemplary), interposed between the pad and its supporting substrate. In some embodiments, the conductive element is plated or otherwise deposited on the pad's supporting structure as a film. In other embodiments, the conductive element may function as the pad's supporting substrate. The element may surround the pad to form a cup-like structure. Preferably the electrically conductive element contacts an electrical lead such as a metal pin that may extend from the element to the underlying solid substrate or to an external terminal. In some embodiments, the element is capable of sufficient Joule heating to raise the temperature in an overlying gel pad by 20 to 75° C. above room temperature.

The "capillary array" or "multicapillary array" of the invention is a plurality of substantially identical capillaries defined by surrounding transparent walls to form capillary tubes wherein the capillary is the axial bore of the tube. In a preferred embodiment, each tube, in outline, approximates a rectangular solid (viz., an object such as a common block, wherein all corners are right angles so that the ends are "squared off"). Each tube has substantially transparent sidewalls. In a preferred embodiment, the axial bore of each tube also has the form of a rectangular solid. In the most preferred embodiment, adjacent capillaries in the array are side-to-side contiguous from end to end, forming a monolith, and the monolith itself approximates a rectangular solid. The aforementioned block-form need not be exact, inasmuch as the ends of each tube and the ends of the monolith as a whole may deviate from the rule to accommodate improvements in sample injection properties and readout properties of the system.

A "diffusion barrier" in the context of the invention is any means for retarding the diffusion of reactants or reaction products from gel spots. By way of example and not of limitation, a zone of relatively non-porous gel surrounding a gel pad would provide a diffusion barrier, as would a hydrophobic surround.

A "dam" refers to a frame or "corral" sized to encompass a region of a two-dimensional array of gel pads. The dam may frame the entire array, or a sub-array thereof. One use for the dam is to retain reagent buffers that may be flooded onto the pad array, typically to protect parts of the array not in use from inadvertently becoming moistened. A cover for the dam is provided to inhibit evaporation and contamination, for example.

The term "fragment" is used variously herein. In one context, it refers to isolated portions of a large nucleic acid, such as a chromosome. In one context, it refers to progeny of such fragments generated in the polymerase chain reaction (PCR). In one context, it refers to fragments extended in length by the Sanger reaction. And in one context, it refers to a part of the system of the invention.

The terms "fused," "fused array, and "fused capillary array" all refer to capillary tubes that lie close enough to each other to permit light beams to traverse from one capillary to the next without refraction such as a light beam encounters in traveling from glass to air, for example. In some cases, fusion is achieved by an actual admixing of the surface layers of two adjacent capillaries. In some cases, glue or other material achieves the effect. The term "monolith" refers to a capillary array characterized by fusion, although it encompasses capillaries arranged in a single row ("MMCA") or in multiple rows ("2D MMCA"), capillaries that do not have the outline of a rectangular solid or square ends, and capillaries that may be non-fused at one or both ends ("split ends").

Laser energy is employed in the methods of the invention to excite the emission of photons by fluorescence ("laser induced fluorescence" or "LIF"). Dyes with fluorescent properties are used to mark or tag specific nucleic acids so that the detection of fluorescent light of a particular color emanating from a particular capillary confers an identity on that nucleic acid.

"Run voltage" refers to the potential difference applied across a capillary to motivate the movement of nucleic acids from a gel pad into and through a capillary to "electrophorese" the nucleic acids. Conventionally, capillary electrophoresis begins from an "injection plug" of sample injected at one end of the capillary. In the invention, there is no such plug. The gel pad serves the dual purpose of a reaction "chamber" and an injection plug.

| Figure Element | Part Number |
|---|---|
| 2D-MMCA | 1 |
| Scanning Laser Beam | 2 |
| Fluoresence Emission | 3 |

Figure 2:
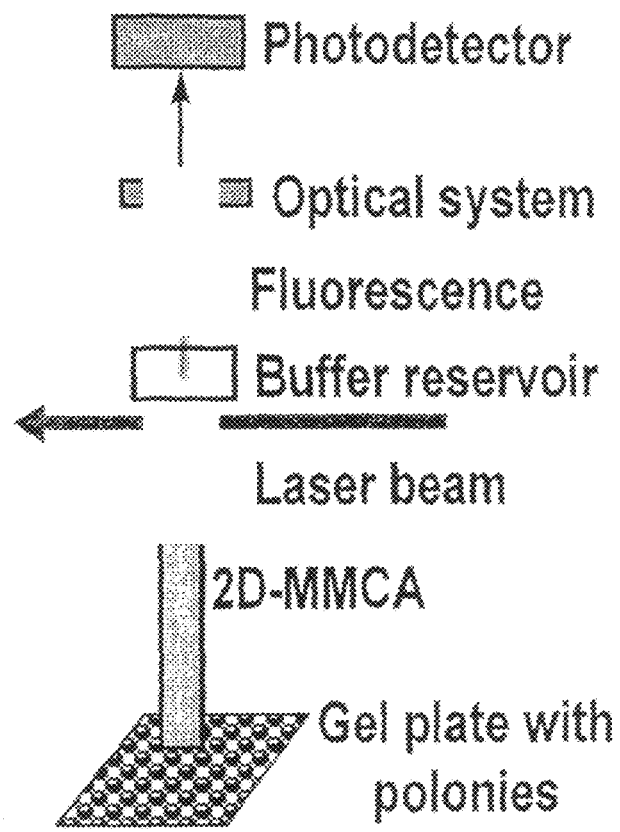

FIG. 2 presents one embodiment of a 2D-MMCA sequencing system. The inlet or loading end of the 2D-MMCA is attached to the surface of the gel plate so that inlets of individual capillaries are exactly above (but preferably not contacting) the spotted polony sites. 8×12 addressable contact pads whose size is equal to the size of the cross section of the 2D-MMCA are lithographically deposited on the plate beneath the gel so that the run voltage is applied to only one pad at a time. In other embodiments, the run voltage may be applied to all pads at once or to a subset. The outlet of the array is immersed into a buffer reservoir, which is preferably transparent. When the electric field is applied, the extension product generated in individual polonies is injected into individual capillaries of the 2D-MMCA directly from the gel surface where it undergoes electrophoretic separation. The separated groups of fragments are detected at the outlet or detection end of the array. The detection is done by exciting the fluorescence of the labeled DNA fragment by a scanning laser beam. Other configurations such as an array of individual laser sources could be used in lieu of a scanning beam. In this preferred embodiment, excited fluorescence is observed from the top of the MMCA through a transparent buffer reservoir, collected by an optical system and projected onto pixels of a photodetector through a rotating filter wheel, for example, a non-limiting means of enabling the photodetector to distinguish colors of light. In other embodiments, the fluorescent light may be collected from a side of the capillary, preferably a side that is not receiving or emitting the excitation beam. The detected data is transferred to a computer for recording and processing.

| Figure Element | Part Number |
|---|---|
| 2D-MMCA | 1 |
| Scanning Laser Beam | 2 |
| Fluoresence Emission | 3 |
| Gel Plate & Polonies | 4 |
| Buffer Reservior | 5 |

-continued

| Figure Element | Part Number |
|---|---|
| Optical System | 6 |
| Photodetector | 7 |

Figure 3:
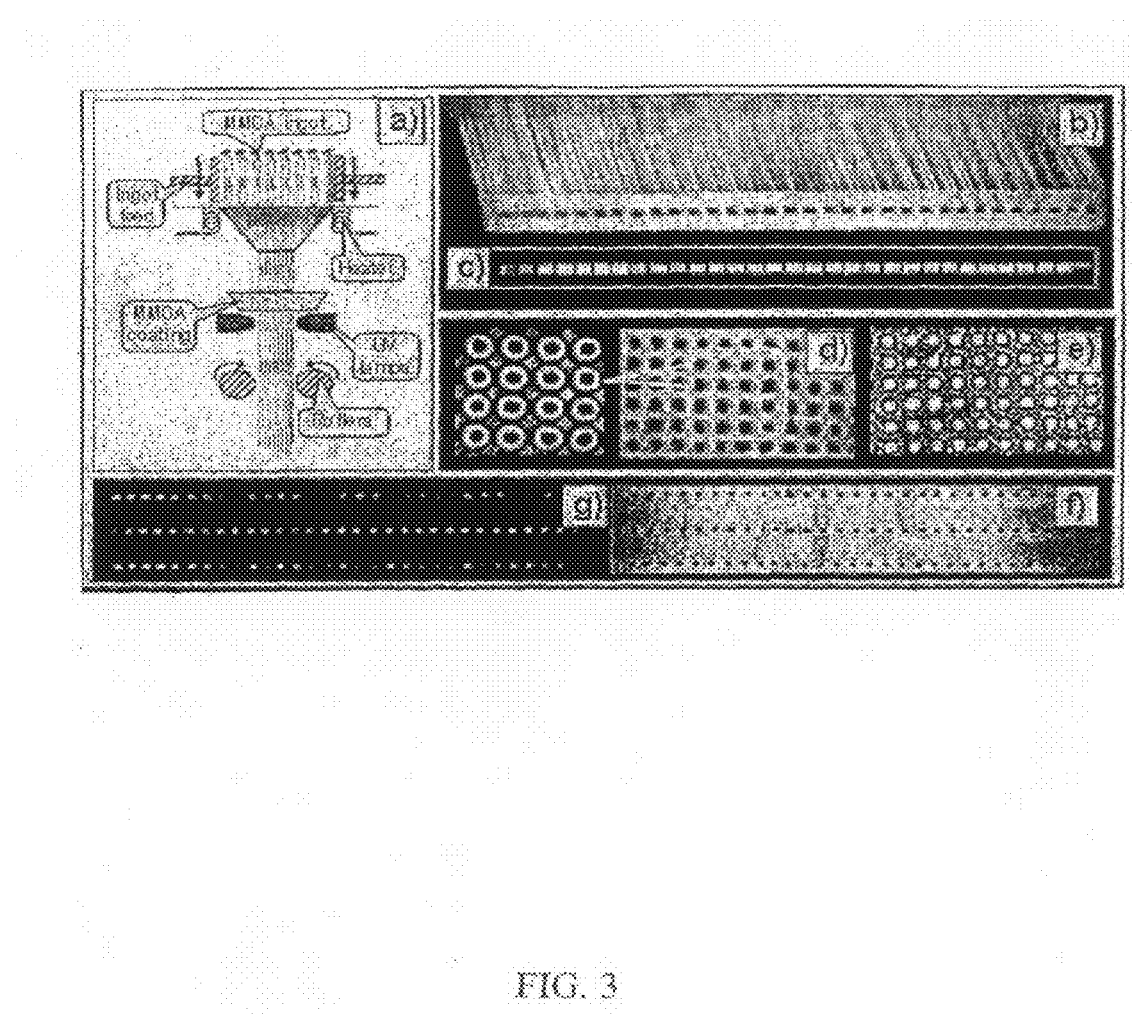

FIG. 3 presents one embodiment of a 2D-MMCA sequencing system. Inset a): Schematic of the general fabrication principle showing an MMCA ingot device. Inset b): Representative illustration of a completed linear MMCA with square capillaries. Inset c): Representative illustration of detectable fluoresence from a top view of a completed linear MMCA with square capillaries. Inset d): Representative illustration of a cross-section of a completed 6×10 2D-MMCA with circular capillaries. Inset e): Representative illustration of detectable fluorescence from a top view of a completed 6×10 2D-MMCA with circular holes. Inset f): Representative illustration of a completed 32×3 2D-MMCA with circular holes. Inset g): Representative illustration of detectable fluorescence from a top view of a completed 32×3 2D-MMCA with circular holes.

| Figure Element | Part Number |
|---|---|
| MMCA Ingot | 8 |
| Ingot Feed | 9 |
| Heater | 10 |
| MMCA Coating | 11 |
| Ultraviolet Lamps | 12 |
| Rollers | 13 |
| 2D-MMCA | 1 |
| Square Capillaries | 14 |
| Round Capillaries | 15 |
| Circular Holes | 16 |

Figure 4:
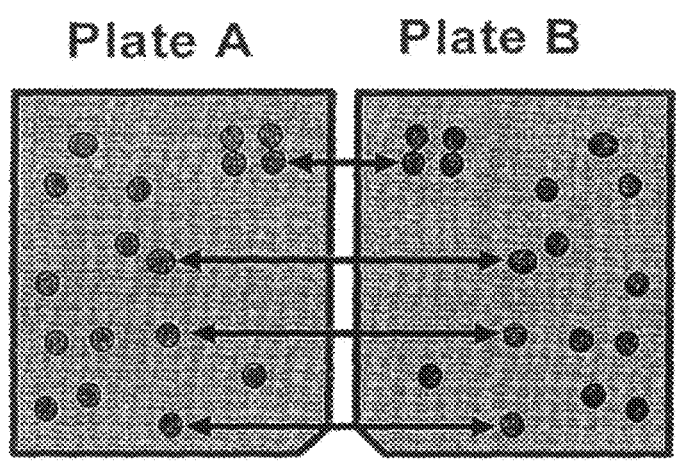

FIG. 4 presents one embodiment of paired plates for the preparation of polonies. Plate A: Well pattern of a first paired plate member. Plate B: Well pattern of a second paired plate member (i.e., having a mirror-image of the well pattern in Plate A). Arrows: Indicating pairs of forward and reverse extended polonies).

| Figure Element | Part Number |
|---|---|
| Plate A | 17 |
| Plate B | 18 |
| Gel Pad Wells | 19 |

Figure 5:
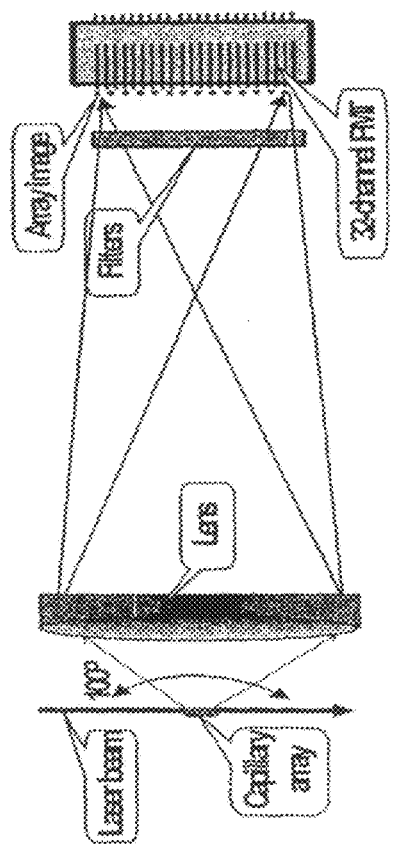

FIG. 5 presents one embodiment of a laser scanning optical system. The multi-capillary array is inserted in a precision holder. A laser beam illuminates the array from the side and excites the fluorescence in the capillaries of the array. The fluorescence image is captured by a lens, passes through a rotating filter wheel and is projected onto a pix elated photodetector. More preferred embodiments are configured to eliminate the need for a filter wheel.

| Figure Element | Part Number |
|---|---|
| 2D-MMCA | 1 |
| Scanning Laser Beam | 2 |
| Lens | 20 |
| Filter Wheel | 21 |
| Photomultiplier Tube | 22 |

Figure 6:
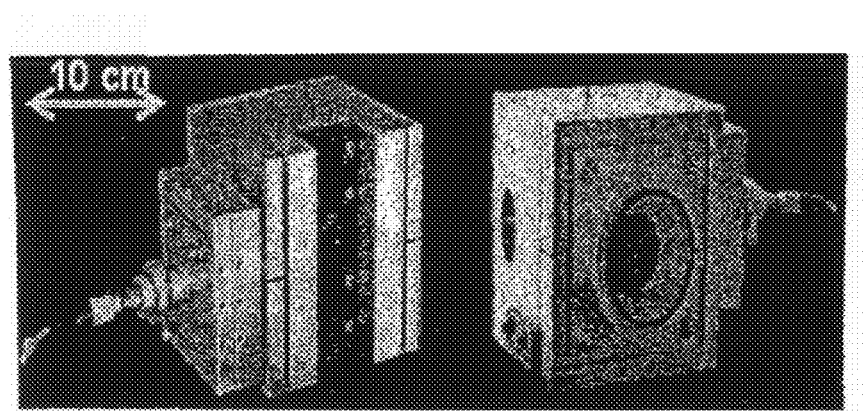

FIG. 6 presents one embodiment of a front and a back view of a custom precision optical reading head.

| Figure Element | Part Number |
|---|---|
| Optical Reading Head, Front | 23 |
| Optical Reading Head, Rear | 24 |
| Input/Output Cable | 25 |
| Lens | 20 |

Figure 7A:
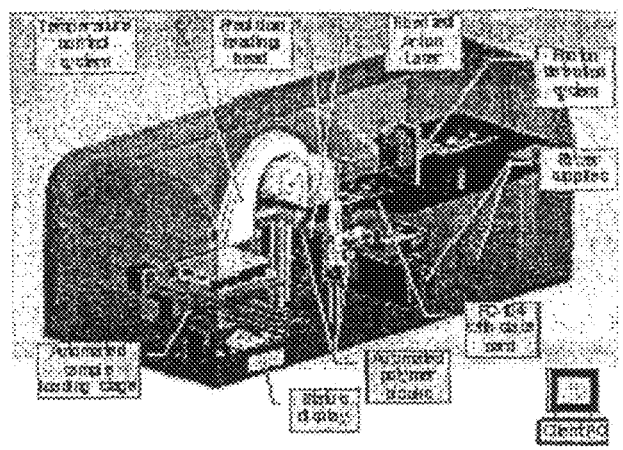
Figure 7B:
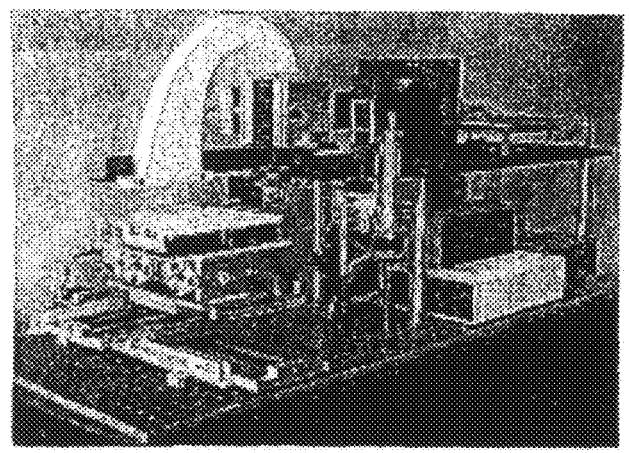

FIG. 7 illustrates one embodiment of a 32-lane DNA sequencer based on single photon detection. Panel A illustrates a 3D model. Panel B shows a 32-lane DNA sequencer. The instrument footprint is 50×25×22 inches.

| FIGURE Element | Part Number |
|---|---|
| 32-Lane DNA Sequencer | 26 |
| Base Level | 27 |
| Upper Level | 28 |
| Temperature Control System | 29 |
| Automated Sample Loading Cassette | 30 |
| Optical Reading System | 31 |
| Laser Device | 32 |
| Display | 33 |
| Photon Detection System | 34 |
| Power Supply | 35 |
| PC104 Control Card | 36 |
| Automated Polymer System | 37 |
| CLIENT Computer | 38 |

Figure 8A:
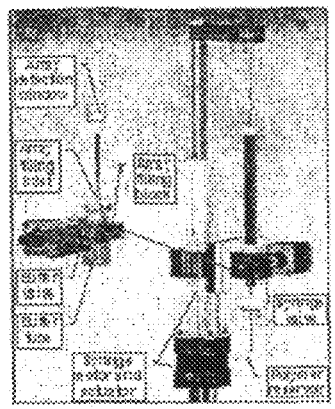
Figure 8B:
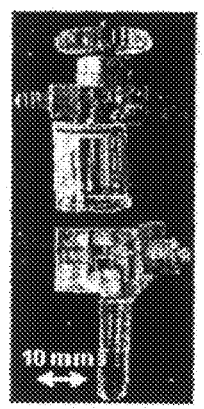
Figure 8C:
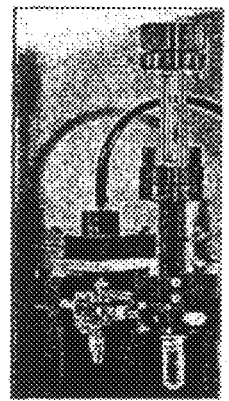

FIG. 8 presents specific embodiments of a 32-lane DNA sequence shown in FIG. 7: Panel A: an automated polymer refilling system; Panel B: A close up of the buffer and syringe blocks; Panel C: A manual refilling system.

| FIGURE Element | Part Number |
|---|---|
| Array Detection Window | 39 |
| Array Filling Inlet | 40 |
| Array Filling Block | 41 |
| Buffer Valve | 42 |
| Buffer Tube | 43 |
| Syringe Valve | 44 |
| Polymer Reservoir | 45 |
| Syringe Motor & Actuator | 46 |

Figure 9:
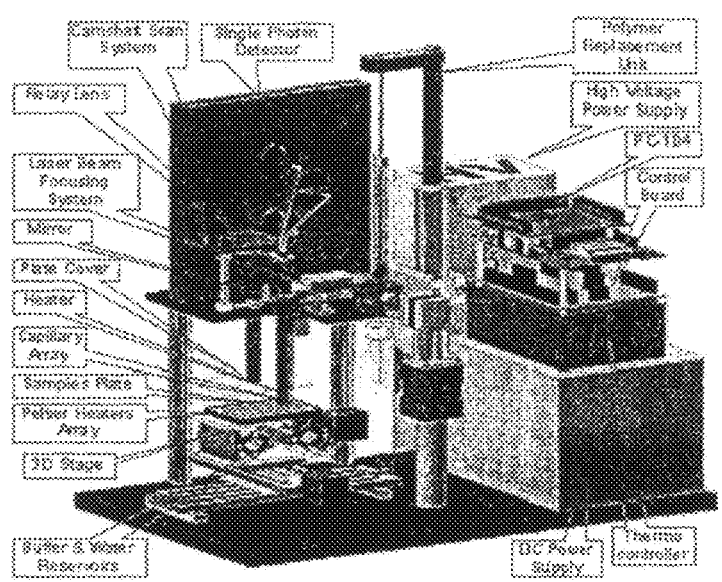

FIG. 9 illustrates one embodiment of an architecture of DNA sequencers based on 2D-MMCA. This illustration presents a 3D model of a multi-lane DNA sequencer.

| FIGURE Element | Part Number |
|---|---|
| Camshaft Scanning System | 47 |
| Relay Lens | 48 |
| Laser Beam Focusing System | 49 |
| Mirror | 50 |
| Plate Cover | 51 |
| Capillary Array Heater | 52 |
| Capillary Array | 53 |
| Gel Pad Slide | 54 |
| Peltier Heater Array | 55 |
| 3D Stage | 56 |
| Buffer & Water Reservoirs | 57 |
| Single Photon Detector | 58 |
| Polymer Replacement Unit | 59 |
| High Voltage Power Supply | 60 |
| PC-104 Control Card | 36 |
| Master Control Board | 61 |
| Thermocontroller | 62 |
| Direct current (DC) Power Supply | 63 |

Figure 10:
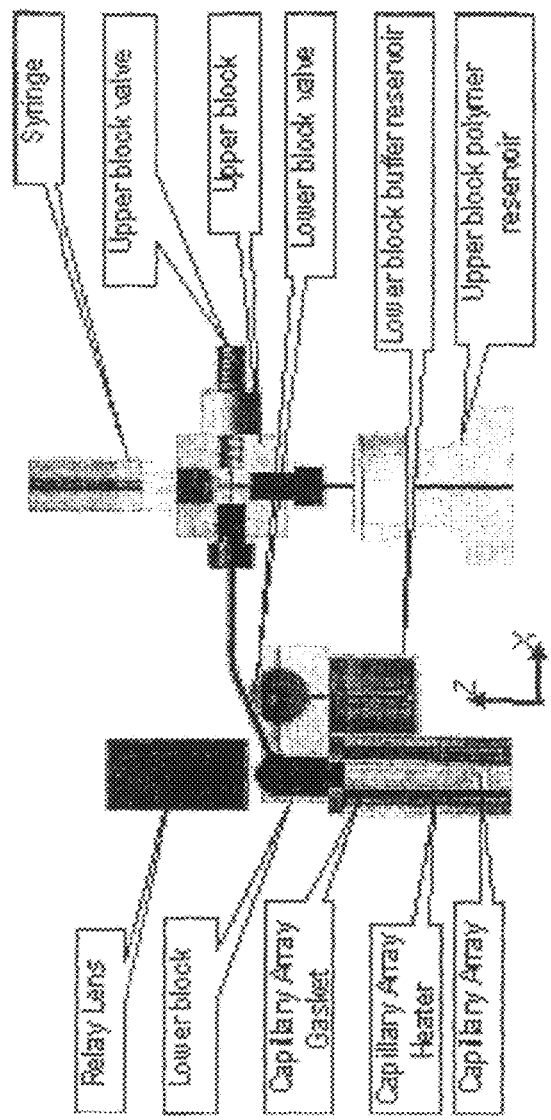

FIG. 10 illustrates one embodiment of a polymer replacement system.

| FIGURE Element | Part Number |
|---|---|
| Relay Lens | 48 |
| Lower Block | 64 |
| Capillary Array gasket | 65 |
| Capillary Array | 53 |
| Polymer Syringe | 66 |
| Upper Block Valve | 67 |
| Lower Block Valve | 68 |
| Lower Block Buffer Reservoir | 69 |
| Upper Block Buffer Reservoir | 70 |

Figure 11:
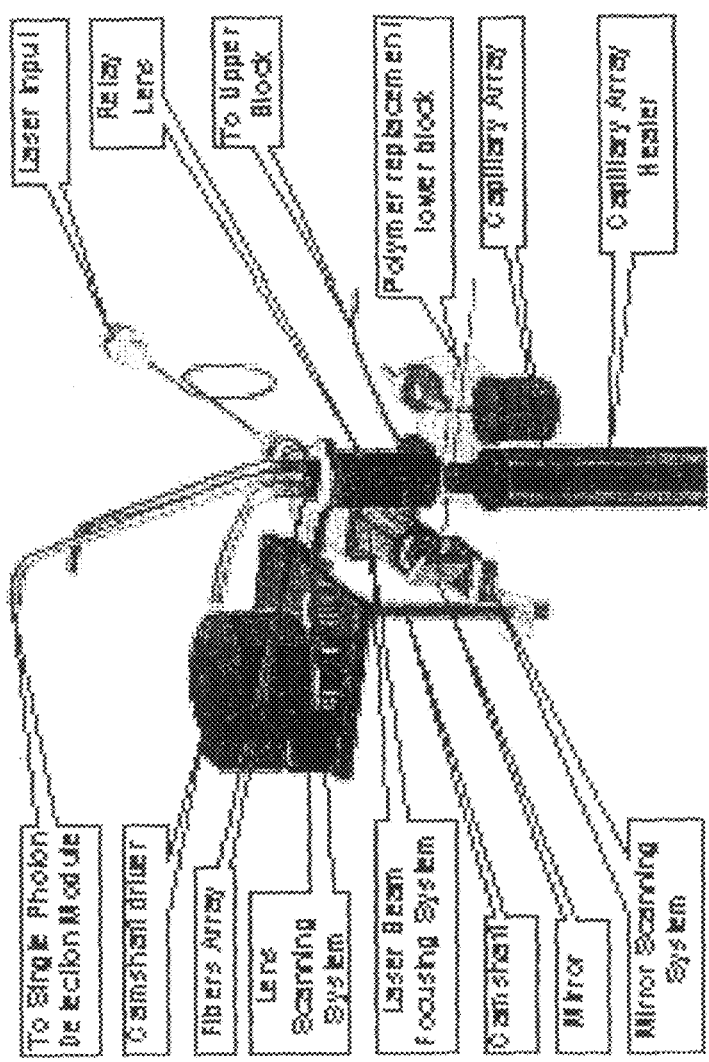

FIG. 11 illustrates one embodiment of a fiberized system for synchronous illumination, collection, and detection of fluorescence in a 2D-MMCA.

| FIGURE Element | Part Number |
|---|---|
| Collection Fibers (lead to SPD) | 71 |
| Camshaft Driver | 72 |
| Collection Fiber Array | 73 |
| Lens Scanning System | 74 |
| Laser Beam Focusing System | 49 |
| Camshaft | 76 |
| Mirror | 50 |
| Mirror Scanning System | 77 |
| Laser Input Cable | 78 |
| Relay Lens | 48 |
| Upper Block Connector | 79 |
| Polymer Replacement Unit | 59 |
| Capillary Array | 53 |
| Capillary Array Heater | 52 |

Figure 12A:
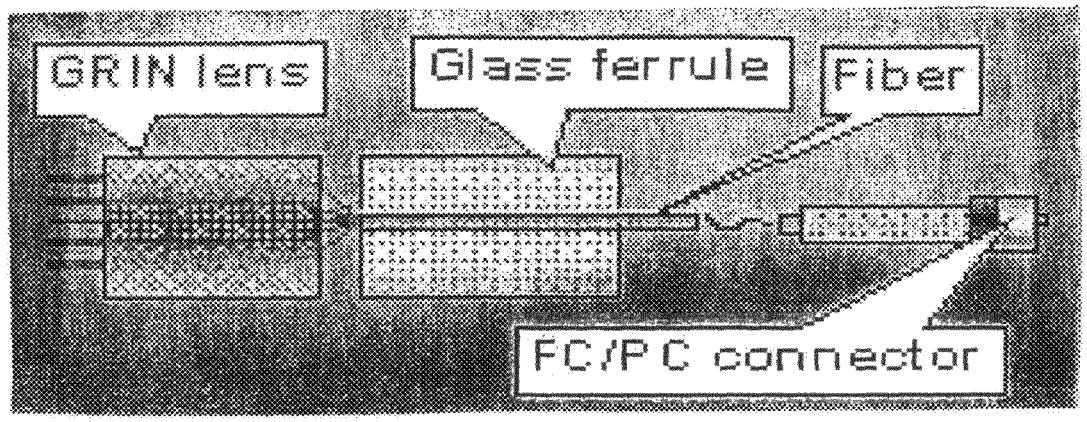
Figure 12B:
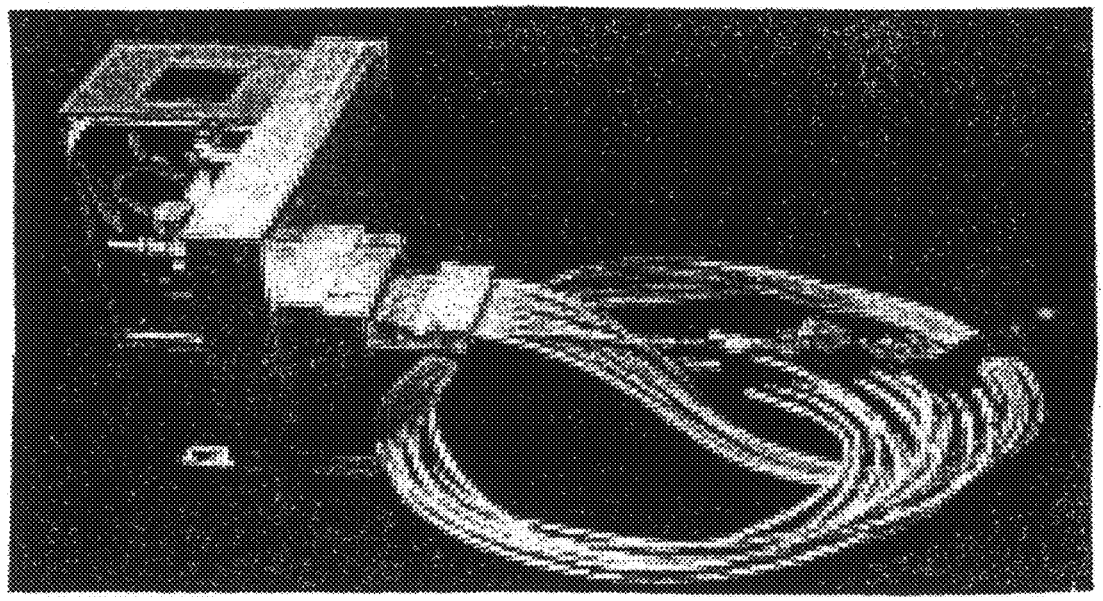

FIG. 12 illustrates a schematic (Panel A) and a photograph (Panel B) of the 4-color fiberized 32-lane filter wheel with encoded filters.

| FIGURE Element | Part Number |
|---|---|
| GRIN Lens | 81 |
| Glass Ferrules | 82 |
| Collection Fiber | 71 |
| FC/PC Connector | 83 |

Figure 13:
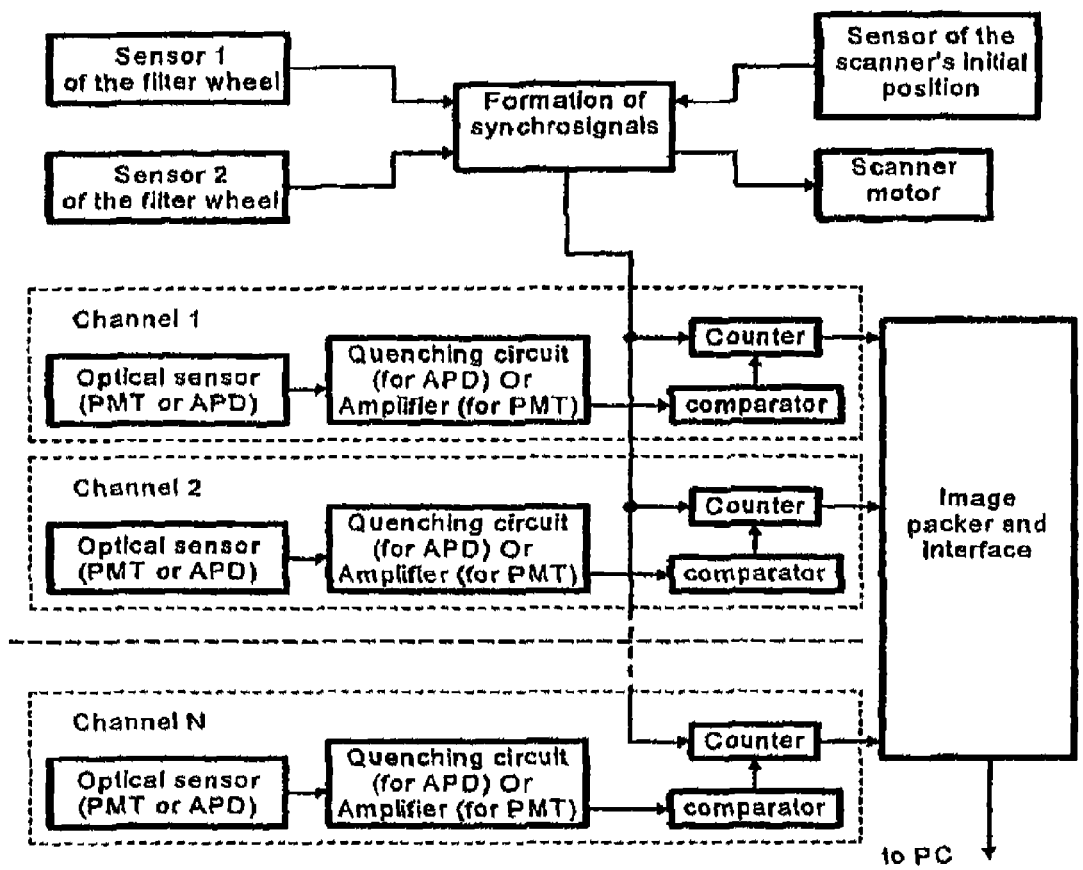

FIG. 13 presents one embodiment of a block diagram for a synchronization system compatible with a 2D-MMCA sequencer.

Figure 14:
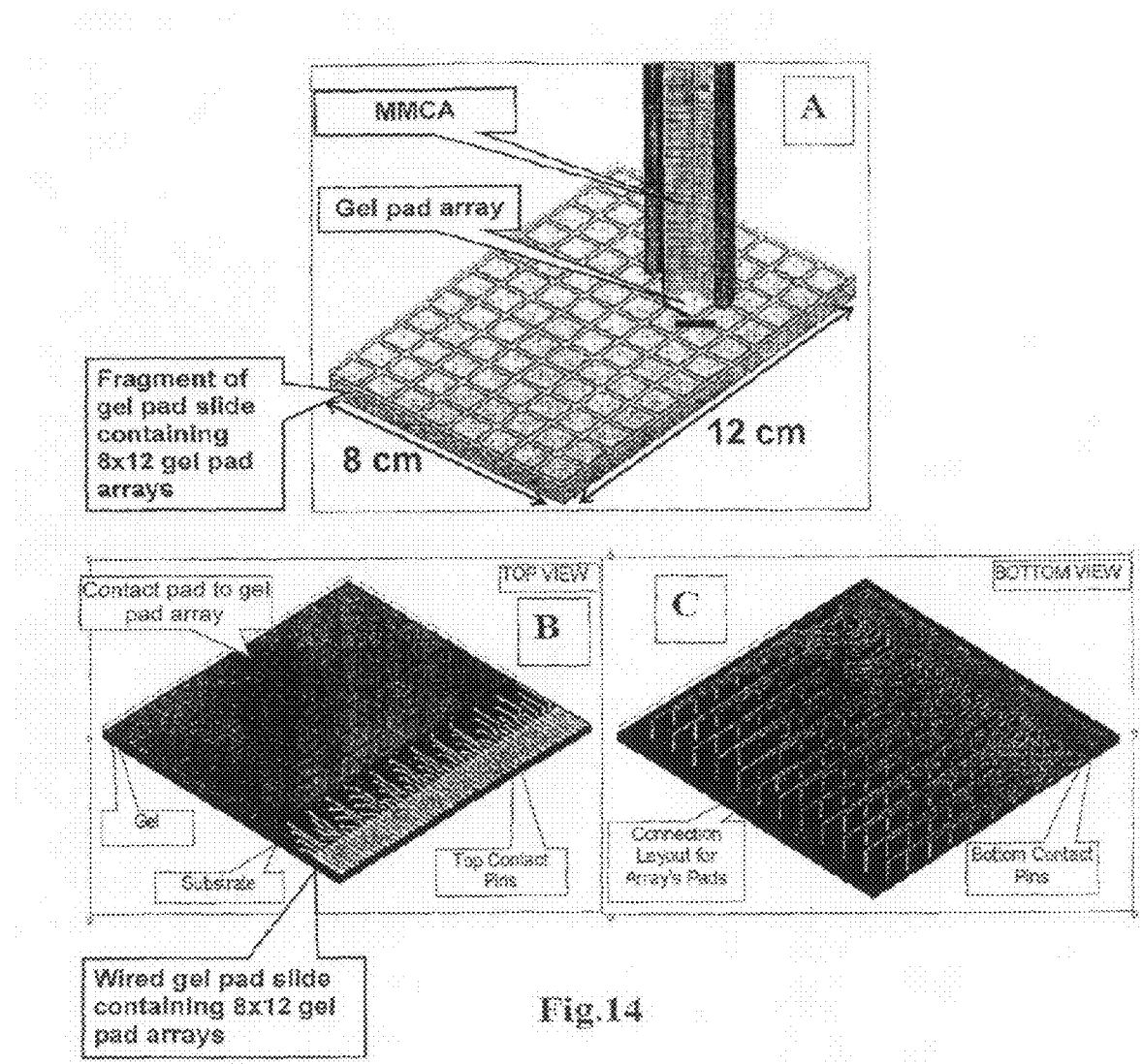

FIG. 14 presents embodiments of an electrokinetic sample injection system. Panel A: A configuration for electrokinetic injection from a gel pad array positioned on the gel slide into 2D-MMCA. Panel B: Pin configuration on a bottom surface of a sample gel plate. Panel C: Pin configuration on a bottom surface of a sample gel plate.

| FIGURE Element | Part Number |
|---|---|
| Array Contact Pads | 84 |
| Gel | 85 |
| Substrate | 86 |
| Top Contact Pins | 87 |
| Array Pad Connection Layout | 88 |
| Bottom Contact Pins | 89 |

Figure 15:
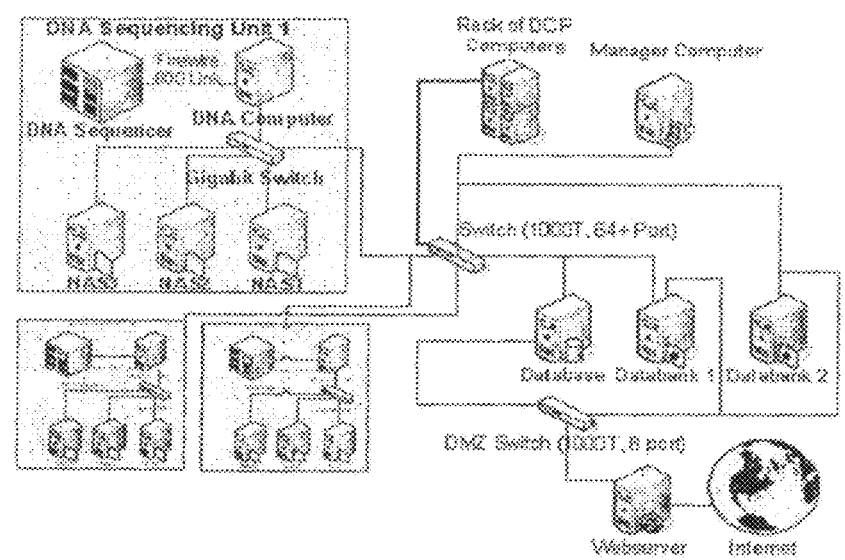

FIG. 15 presents one embodiment of a flowchart showing a computer controlled data acquisition, management, and tracking system that is compatible with 2D-MMCA CE.

Figure 16:
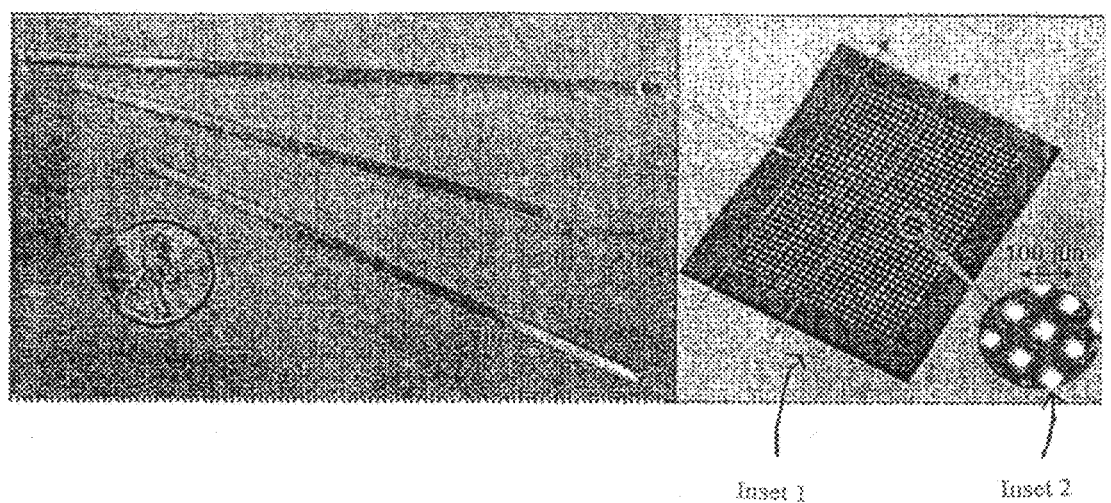

FIG. 16 presents several embodiments of representative 32×24 monolith multi-capillary arrays (MMCAs). A lengthwise depiction of several 2D-MMCAs in size contrast with a US penny. Inset 1: An enlarged 2D-MMCA array cross-section. Inset 2: A close-up showing a representative 2D-MICA array region showing the spatial arrangement of square capillaries.

| FIGURE Element | Part Number |
| --- | --- |
| 2D-MMCA | 1 |
| 2D-MMCA Crosssection | 90 |
| Square Capillaries | 14 |

Figure 17:
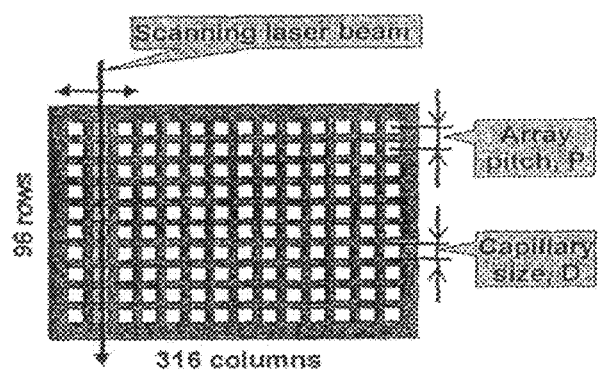

FIG. 17 presents one embodiment of a 96×316 capillary array demonstrating row-by-row laser beam scanning (Arrows). P=array pitch (i.e., the center-to-center distance between reaction wells or, more generally, between any adjacent elements in a regular array); D=capillary size (length or width if square; diameter if circular).

| FIGURE Element | Part Number |
| --- | --- |
| 2D-MMCA Crosssection | 90 |
| Scanning Laser Beam | 2 |
| Square Capillaries | 14 |

Figure 18:
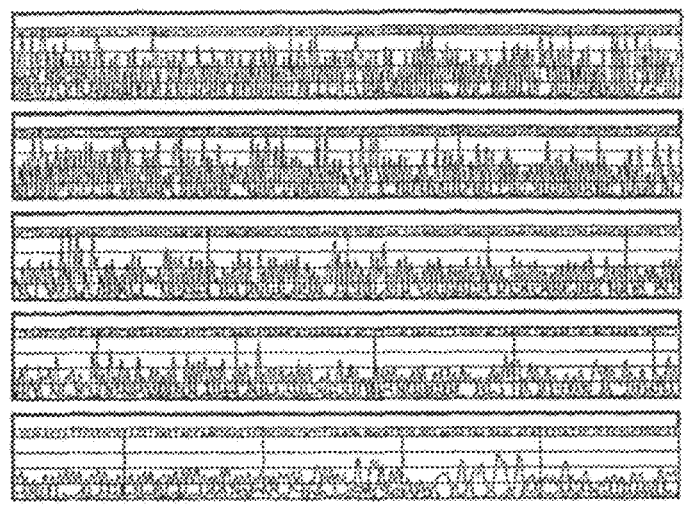

FIG. 18 presents an exemplary sequencing trace obtained from a 1:100 diluted BigDye® DNA sequencing standard (Applied Biosystems, Inc. CA) with 0.5 mW illumination power.

Figure 19:
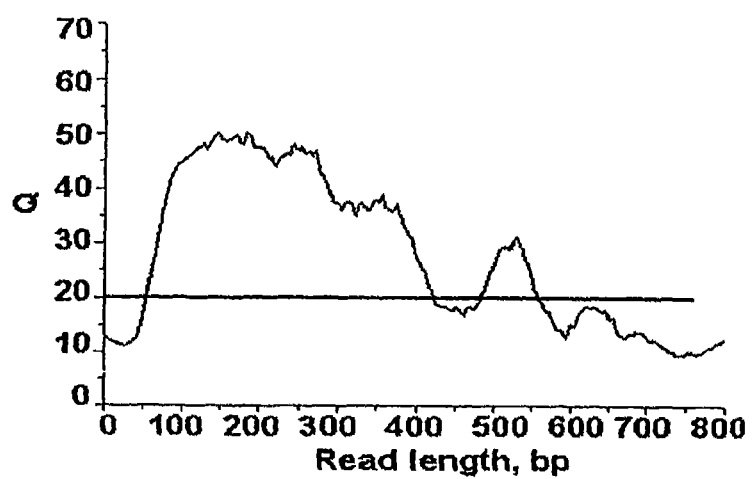

FIG. 19 presents exemplary data showing more than a 500 base read length at 99% accuracy (see, a Q (quality) factor plot, Q>20) for the 1:100 dilution data presented in FIG. 18.

Figure 20:
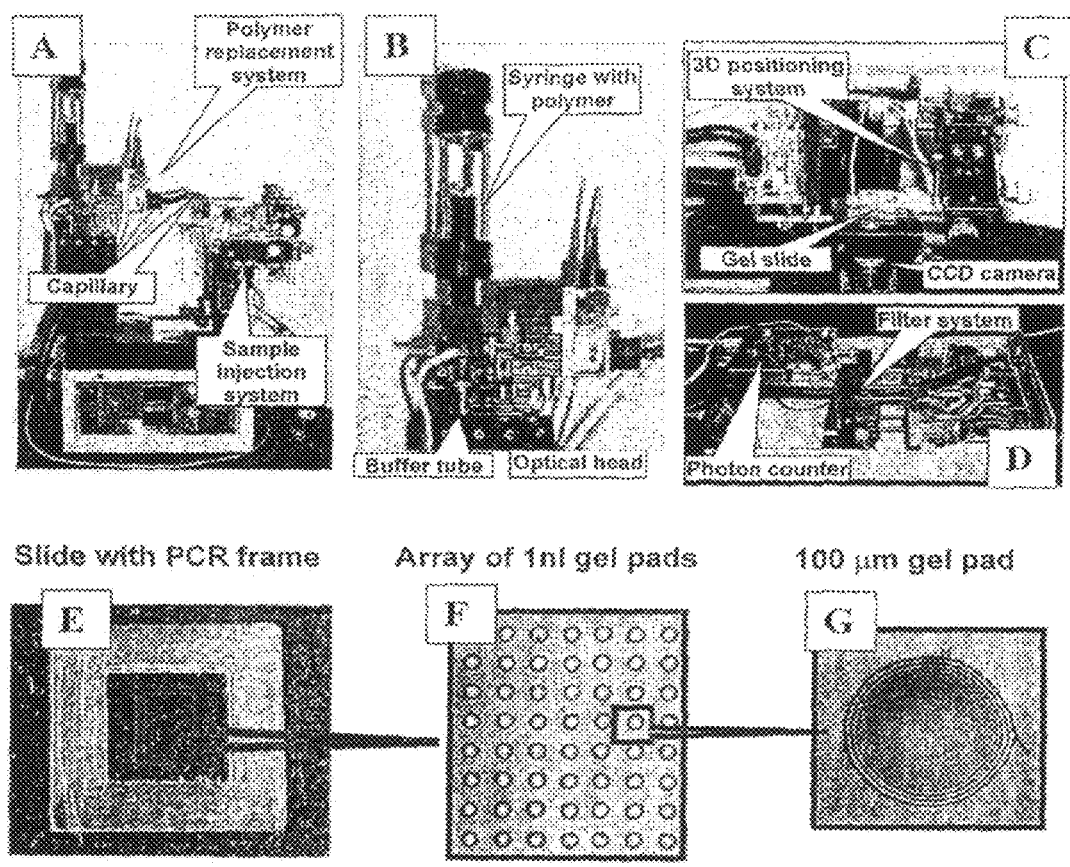

FIG. 20 presents several embodiments of a DNA sequencer configured with an electrokinetic injection system. Panel A: General view showing a polymer replacement system, a capillary and an electrokinetic sample injection system. Panel B: A close-up view of a polymer replacement module, buffer tube, and an optical head. Panel C: A close-up view of a gel-slide positioning system (i.e, 3D), a gel slide, and a charged coupled device (CCD) camera; Panel D: A close-up view of a photon detection system comprising a photon counter and a filter wheel system. Panel E: A close-up view of a slide with an attached PCR frame. Panel F: Exploded inset from Panel E showing a gel pad array. Panel G: Exploded inset from Panel F showing an individual gel pad.

| FIGURE Element | Part Number |
| --- | --- |
| Polymer Replacement Unit | 59 |
| Capillary Array | 53 |
| Electrokinetic Injection System | 91 |
| Polymer Syringe | 66 |
| 3D Positioning System | 92 |
| Gel Pad Slide | 93 |
| CCD Camera | 94 |
| Filter Wheel System | 95 |
| Photon Counter | 92 |
| Optical Reading System | 31 |
| Buffer Tube | 93 |
| PCR Frame | 102 |
| Gel Pad Array | 103 |
| Individual Gel Pad | 104 |

Figure 21:
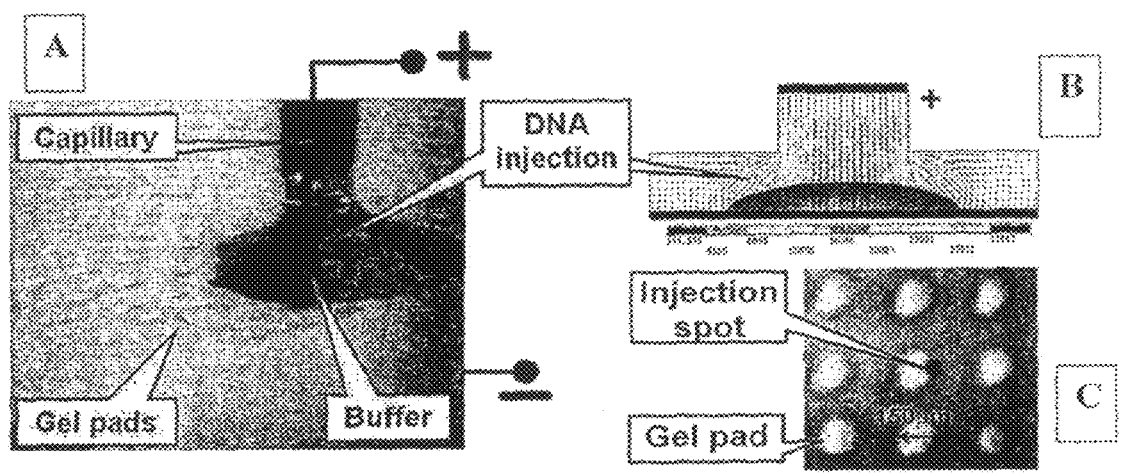

FIG. 21 illustrates one embodiment of a field-flow electrokinetic injection system. Panel A: General instrument configuration of a capillary, gel pad slide and interface buffer layer, and electrical contacts to the slide surface (−) and to the capillary (+). Panel B: Calculated distribution of an electric field. Panel C: An $In_2O_3$ coated glass substrate with gel pads and a dark area of reduced indium (indicating injection current distribution over the slide surface) showing the injection spot. Injection parameters: 1 kV, 10 s, 100 mm distance between the gel pad slide and the capillary inlet, capillary ID=50 µm, OD=300 µm.

| FIGURE Element | Part Number |
| --- | --- |
| Capillary Array | 53 |
| Gel Pad Slide | 54 |
| Buffer Block | 94 |
| Injection Spot | 95 |
| Gel Pad | 96 |

Figure 22:
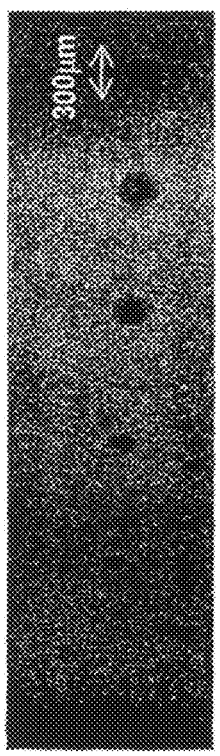

FIG. 22 presents exemplary data showing the determination of optimal electrokinetic injection spot size based upon the capillary-to-slide distance (d). From left to right: d=50 µm, 100 µm, 150 µm, 200 µm, 250 µm, and 300 µm.

| FIGURE Element | Part Number |
| --- | --- |
| Injection Spots | 95 |

Figure 23:
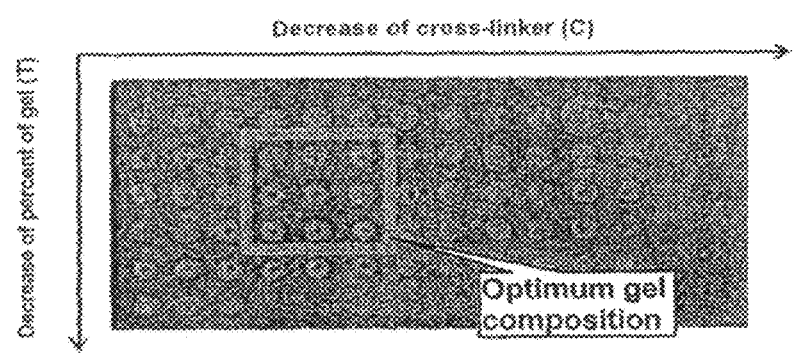

FIG. 23 presents exemplary data showing the relationship of cross-linkers and gel monomer (T) to produce an optimal gel composition to support electrokinetic injection. Framed area corresponds to the region of optimal gel compositions. Non-optimal compositions yield overlarge, "loose" gels (top and left) or small, relatively non-porous gels (lower right). Each gel pad=2 nanoliter volume.

Figure 24A:
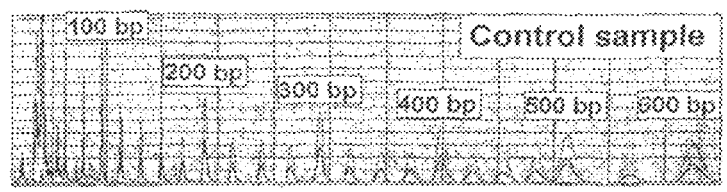
Figure 24B:
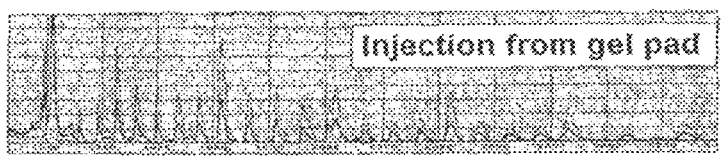

FIG. 24 presents exemplary data showing effective capillary electrophoresis following electrokinetic injection of a DNA fragment. Panel A: Separation traces obtained after conventional injection of a genetic ladder (ILS, Promega, WI) from a tube into a capillary; Injection Conditions; 10 kV, 3 s. Panel B: Separation traces obtained after electrokinetic injection of the same sample from a gel pad into a capillary. Injection conditions; 2 kV, 10 s.

Figure 25:
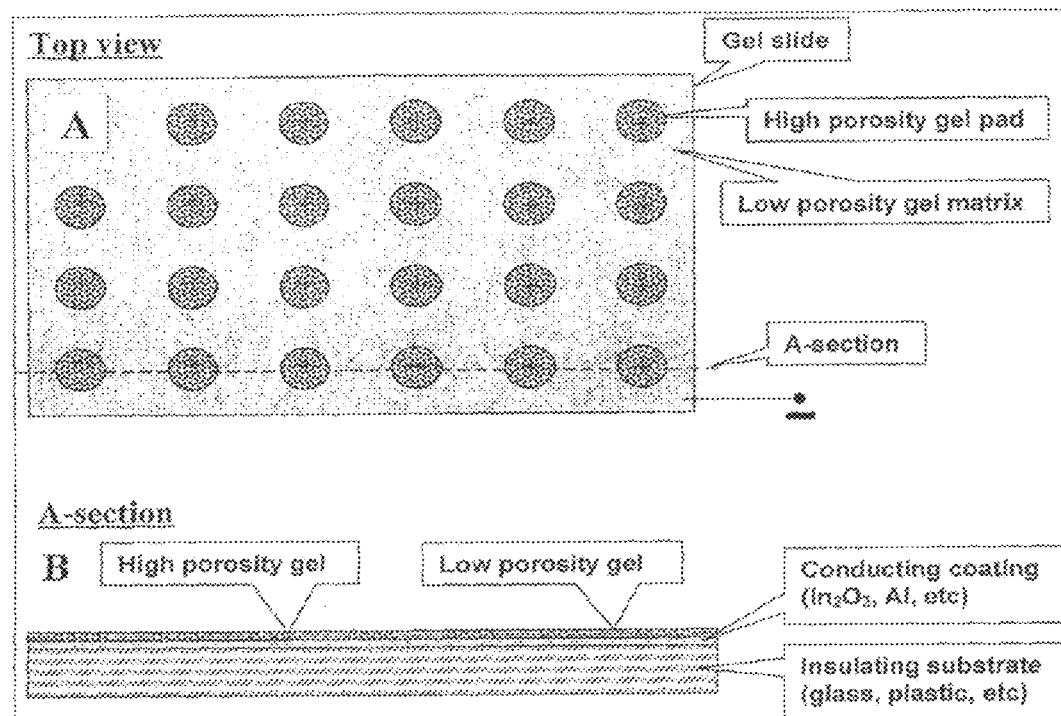

FIG. 25 presents one embodiment of an isolated gel pad. Panel A: Schematic top view representation of a gel slide showing the spatial arrangement between a high porosity gel pad and a low porosity gel matrix, and electric contacts to the slide surface (−) and to the individual gel pads (+). Panel B: Schematic cross-sectional representation of the compositional structure of a gel slide comprising an electrically conductive element or coating, high porosity gel pads, and a low porosity gel matrix.

| FIGURE Element | Part Number |
| --- | --- |
| Gel Pad Slide | 54 |
| High Porosity Gel Pad | 97 |
| Low Porosity Gel Matrix | 98 |
| Conducting Coating | 99 |
| Insulating Substrate | 100 |

Figure 26:
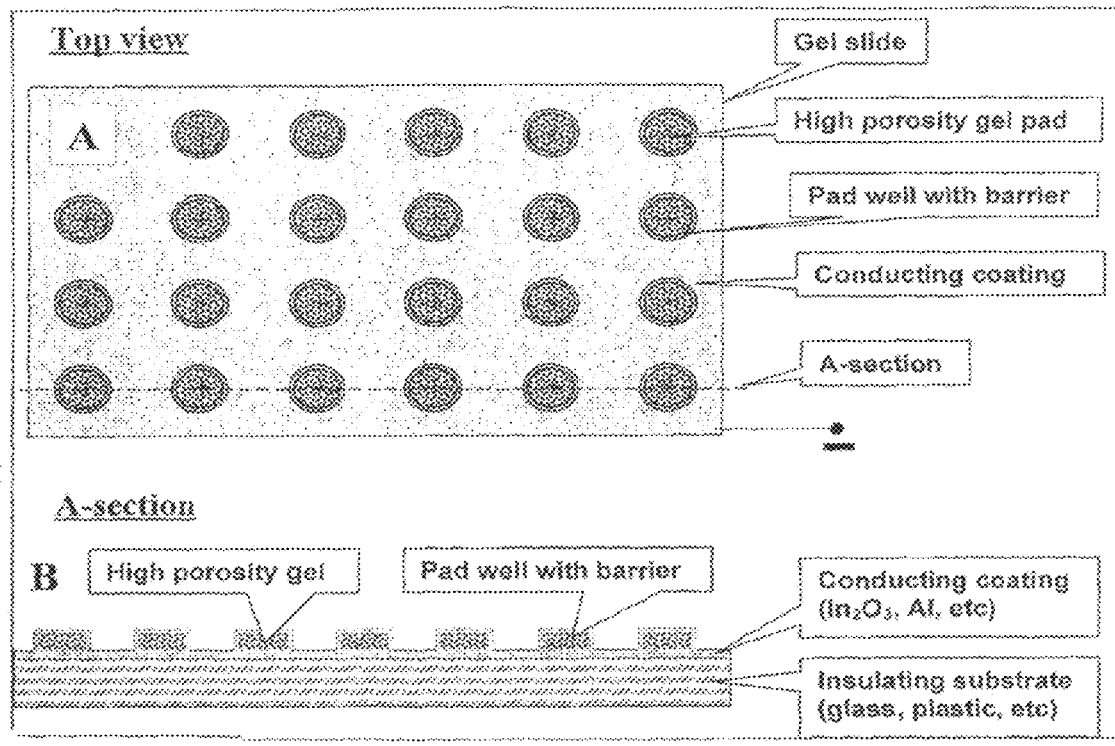

FIG. 26 presents one embodiment of an isolated gel pad. Panel A: Schematic top view representation of a gel slide showing the spatial arrangement between high porosity gel pads surrounded by barriers, and electric contacts to the slide surface (−) and to the individual gel pads (+). Panel B: Schematic cross-sectional representation of the compositional structure of a gel slide comprising high porosity gel pads surrounded by barriers.

| FIGURE Element | Part Number |
|---|---|
| Gel Pad Slide | 54 |
| High Porosity Gel Pad | 97 |
| Gel Pad Barrier | 101 |
| Conducting Coating | 99 |
| Insulating Substrate | 100 |

Figure 27:
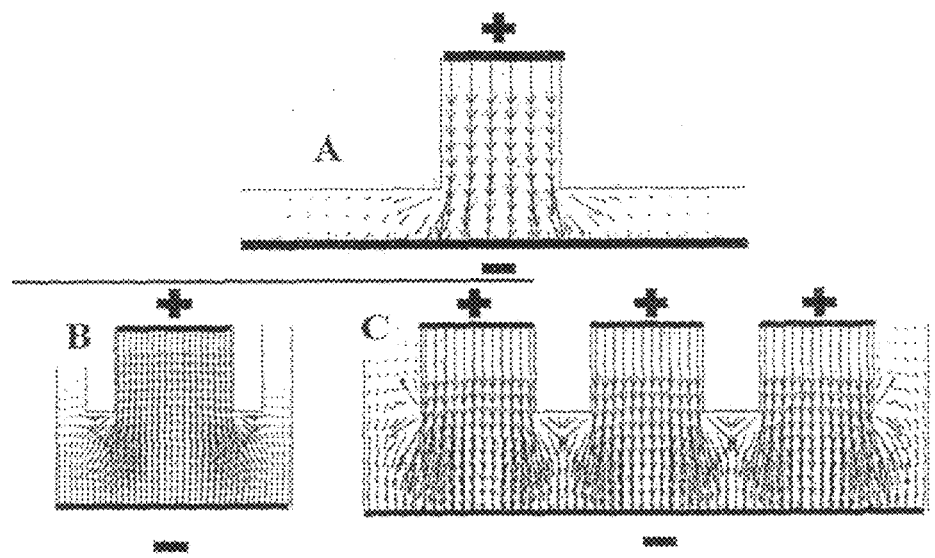

FIG. 27 presents several alternative embodiments for the generation of electrokinetic field flows depicted using computer simulations. Panel A: An isolated capillary configuration. Panel B: A single capillary surrounded by walls configuration. Panel C: A fragment or portion of a capillary array configuration.

Figure 28:
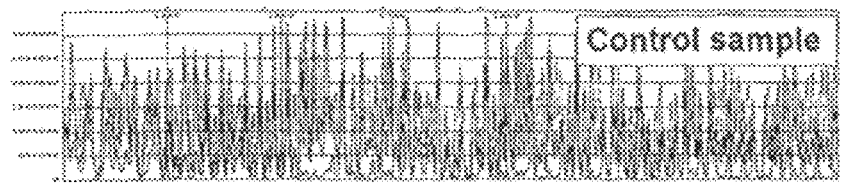
Figure 28:
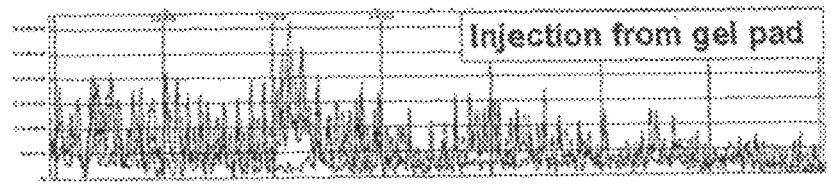

FIG. 28 presents exemplary data showing separation traces of the first 200 bases obtained after conventional and electrokinetic injection of BigDye-3.1 DNA sequencing standard into a 50 cm capillary. Panel A: Control injection from a tube; Injection conditions: 3 kV, 10 s. Panel B: Electrokinetic injection from a gel pad. Injection conditions: 1 kV, 10 s.

Figure 29:
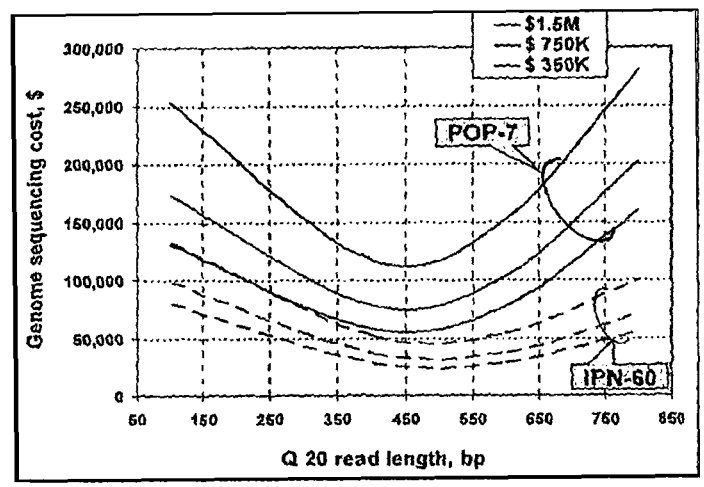

FIG. 29 presents exemplary data showing the relationships between DNA Sequencer costs, Q20 read length, and total cost to sequence a single genome. Solid lines: POP-7 separation media. Dashed lines; IPN-60 separation media.

DETAILED DESCRIPTION

The present invention relates to nucleotide sequencing. In one embodiment, the sequencing is performed using capillary electrophoresis. In one embodiment, the capillaries are arranged in a fused array. In one embodiment, the fused capillary array is loaded with sequencing product using electrokinetic technology.

I. Nucleotide Sequencing Methodologies

Numerous technologies that are capable of sequencing nucleic acids have been reported. (Tillib & Mirzabekov, 2001; Shendure et al., 2004). It has been suggested to subdivide these technologies into five major groups.

A. Microelectrophoretic Sequencing

This technology is based upon classical Sanger methods using cycle sequencing reactions producing dideoxyribonucleotide triphosphate- (ddNTP-) terminated fragments followed by capillary electrophoresis ("CE"). (Sanger et al., 1977) Heavily drawing on the advances of microfabrication techniques developed by the semiconductor industry, the groups of Dr. Mathies and BioMEMS lab are using lithography-based multiplexing, integration and miniaturization to create hundreds of microchambers and microchannels in a single on-chip device that integrates DNA amplification, purification and sequencing. (Lagally et al., 2001; Paegel et al., 2003). High-throughput CE methods (i.e., for example, on-chip) can achieve comparably high accuracy and a read length of ~800 bp. (Koutny et al., 2000). However, one disadvantage regarding on-chip technologies is the potential to produce cost savings of only ~10-fold higher than commercial CE-based systems. The on-chip technology is further limited by its innate planar nature, and production-ready, large-scale high throughput, microfabricated devices still have long (40 cm) channels. Therefore, achieving a 100-fold cost reduction might require radical and as yet unknown changes in the underlying engineering of microelectrophoretic sequencers, which would in turn require unforeseeable time and investment. Besides microfabrication technologies, the others in the list are in relatively early stages of development and it is difficult to judge when any of them will become truly practical, not to mention to assess their costs.

B. Sequencing by Hybridization

This technology is based on differential hybridization of oligonucleotide probes to recover a target DNA sequence. Two main approaches have been reported: i) immobilizing the target DNA; and immobilizing the oligonucleotide probes (Affymetrix and Perlegen, respectively). The sequencing by hybridization strategy has been applied to both re-sequencing and de novo sequencing protocols. (Khrapko et al., 1989; Lipshutz et al., 1995; Drmanac et al., 1998; Patil et al., 2001). The main disadvantages of this technology are: i) a relatively short read-length (~25 bp) due to the limited length of the query probe; ii) significant sample-preparation steps; and cross-hybridization of probes to the incorrect targets due to repetitive elements or chance similarities. (Lipshutz et al., 1995). The latter factor may result in a very substantial loss of genetic information, e.g., such as over 50% of chromosome 21. (Patil et al., 2001).

C. Cyclic Array Sequencing of Amplified DNA

This technology is based on multiple cycles of enzymatic manipulations of spatially separated and amplified DNA fragments. Early developments of these methods involved electrophoresis, which essentially limited their throughput. Therefore, presently these methods evolve along an "electrophoresis-free" path. (Ronaghi et al., 1996; Ronaghi, 2001; Pourmand et al., 2002; Mitra et al., 2003; Kartalov & Quake, 2004). For example, each cycle of enzymatic manipulations detects only one or a few bases, but thousands to millions of fragments are processed in parallel.

All methods of this kind involve an amplification step necessary for obtaining a sufficient signal for detection. There are several approaches to DNA amplification: i) a PicoTiter® assay can plate hundreds of thousands of PCR reactions in picoliter-volume wells (Leamon et al., 2003); ii) the PCR colony, or "polony" technology (Mitra & Church, 1999); strand displacement amplification (SDA) (Westin et al., 2000); and iv) PCR-based amplification in oil-aqueous emulsions followed by magnetic bead capturing (BEAM method) (Dressman et al., 2003). These methods involve multiplexing in space and time, isolated amplification of single molecules, and avoidance of bacterial cloning. Specific amplification approaches have been Combined with specific sequencing methods. For example, a 'PicoTiter® plate' is usually combined with pyrosequencing (Ronaghi et al., 1996; Ronaghi, 2001; Leamon et al., 2003). Further, a "polony" technology may be combined with 'fluorescent in situ sequencing' (FIS-SEQ) (Mitra et al., 2003). SDA, however, may be combined with 'massively parallel signature sequencing' (MPSS) (Brenner et al., 2000) or hybridization (Lage et al., 2003).

In both FISSEQ and pyrosequencing, progression through the sequencing reaction is externally controlled by the stepwise (i.e., for example, cyclical), polymerase-driven addition of a single type of dNTP to an array of amplified, primed templates. MPSS is based on cycles of restriction digestion and ligation without thermocycling with polymerase. Although cyclic array sequencing methods have a potential for genome sequencing at a very low cost, the short-term prognosis is rather unclear. In order to reach de novo sequencing capability, these techniques have insufficient read length. So far, the FISSEQ read length does not exceed eight (8) base pairs, and the pyrosequencing technique does not exceed fifty (50) base pairs. Another problem of these methods is their low accuracy, especially in the case of homopolymeric sequences, due to dephasing—the progressive loss of synchronization between templates.

C. Cyclic Array Sequencing on Single DNA Molecules

This technology is presently at a very early stage of development. (Korlach et al., 2001; Levene et al., 2003; Braslaysky et al., 2003) (Braslaysky et al., 2003). Although unproven, this technology is expected to eliminate amplification and its associated biases, as well as increase read length and accuracy.

D. Non-Cyclical, Single-Molecule, Real-Time Methods

This technology is in its infancy and requires significant improvements in core engineering and signal to noise ratios to achieve the required single base resolution at a long read length. In general, single-molecule sequencing methods face a number of scientific and technological problems, and has been suggested to require substantial basic research and development, and taking at least a decade to achieve re-sequencing and de novo sequencing of human-size genomes. (Meller et al., 2000; Deamer & Akeson, 2000; Winters-Hilt et al., 2003).

II. Monolith Multi-Capillary Arrays

The above-described disadvantages of many nucleotide sequencing techniques may be overcome by various embodiments of the present invention. In particular are the advantages of long read lengths and low cost, coupled with high accuracy.

In one embodiment, the present invention contemplates a specific geometry of a vessel for 2D-MMCA CE that, for the first time, brings CE DNA sequencing throughput to a level comparable with cyclic array sequencing technology.

In one embodiment, a 2D-MMCA is used in conjunction with at least one immobilized DNA colony. In one embodiment, a sequencing product is electrokinetically injected from the gel into a 2D-MMCA by "floating" the product on a current flowing in an electric field so that the gel and the capillary remain uncoupled. In one embodiment, the array ends are unsplit. Although it is not necessary to understand the mechanism of an invention, it is believed that these aspects greatly simplify the design of the DNA sequencer.

In one embodiment, the present invention contemplates clone tracking based upon the addressed positions of polonies.

In one embodiment, the present invention contemplates a method for forward and reverse sequencing of the same clone of 3-5 kb DNA fragments. In one embodiment, forward-reverse sequencing yields read-pair information, thereby facilitating de novo DNA sequencing.

In summary, the present invention contemplates various embodiments including, but not limited to:

1. An integrated system performing CE-LIF in 2D-MMCA with DNA sample preparation and tracking using immobilized colonies of single or multiple template/DNA molecules. This embodiment includes, among other things:
   1.1. Direct injection from a surface of immobilized colonies without need for split ends; without need for male-female kind of connection with sample vessel; and without cross-talk (due to field flow of current from an individual sample to an individual capillary).
   1.2. Injection without need to form first an injection plug in a capillary, that is, immobilized colony serves as injection plug.
   1.3. Detection unit integrated with buffer-polymer loading unit.
2. Sample preparation and tracking approach, e.g., mirror pairs of sample/colony plates, allowing to sequence from both ends of the same template/amplicon and thus create read-pairs of long fragments.
3. Fluorescence excitation and detection can also be carried out based on multicolor modulation excitation and emission detection. U.S. Pat. No. 5,784,157 (herein incorporated by reference).

A. Systems Analysis

In one embodiment, the present invention contemplates a 100-fold reduction of the DNA sequencing cost compared to highly optimized, large scale DNA sequencing facilities. Although it is not necessary to understand the mechanism of an invention, it is believed that there is an approximately even cost distribution between consumables, labor, instrumentation, and operational cost of sequencing facility costs. In one embodiment, the present invention contemplates a 100-fold reduction of all major cost components.

The previously reported sequencing technologies discussed above fall into two major categories: (i) those that presently offer very high cost savings in DNA sample preparation, but have rather very short read length and insufficient base calling accuracy (i.e., for example, sequencing by extension), and (ii) those based on CE in microfabricated devices, which can presently provide both highly accurate reads of several hundred bases and significant reagent savings, but offer only ~10-fold increased throughput compared to commercial instruments, which is insufficient for the targeted 100-fold cost reduction.

Although it is not necessary to understand the mechanism of an invention, it is believed that one factor limiting throughput of CE-based technologies is the linear (or planar) geometry of existing multi-capillary arrays. For example, in large scale machines, the CE lanes are packed in a row of individual capillaries which allows obtaining the most efficient fluorescence excitation and collection from the array. Alternatively, in microfabricated devices, the CE microchannels are fabricated in one plane due to fundamental constraints of the fabrication technology. This linear architecture constrains the number of CE lanes that can be illuminated by one laser source (either simultaneously or sequentially) and ultimately limits one of the most important characteristics of the throughput of sequencing facilities: number of bases per instrument per second. Even for highly optimized DNA sequencing centers, this number is ~24 base pairs per second per instrument.

One approach to achieve a 100-fold cost reduction is an integration into one system of the main advantages offered by previously reported nucleotide sequencing technologies. In one embodiment, the present invention contemplates methods comprising a highly integrative approach to DNA sample preparation in conjunction with a CE separation system modified to allow an additional 10-fold increase in throughput when compared to microfabricated devices. Although it is not necessary to understand the mechanism of an invention, it is believed that such an increase can be achieved by changing the geometry of the multi-capillary arrays from linear to 2-dimensional (see (Gorfinkel et al., 2002; Alaverdian et al., 2002)).

Figure 1:
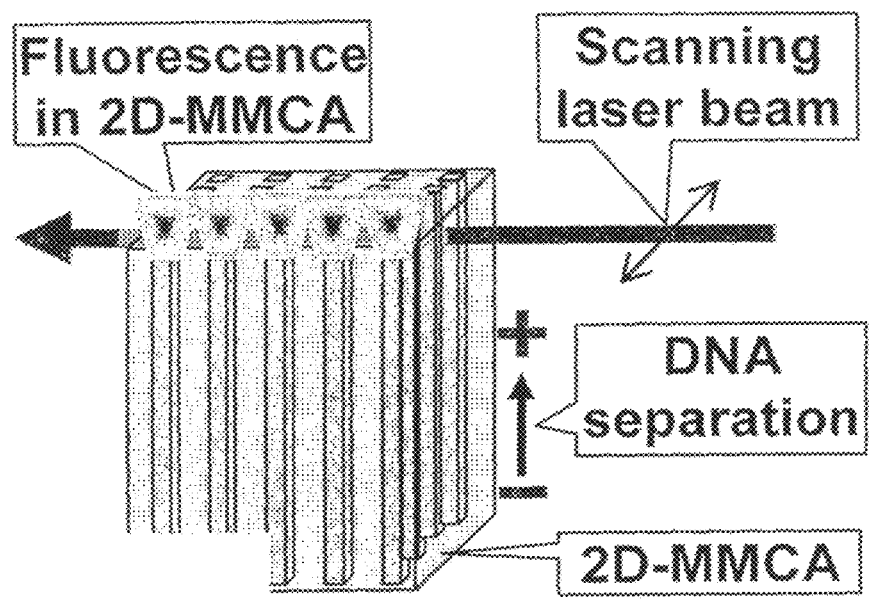
FIG. 1 presents one embodiment of a 2D-MMCA sequencing system depicting: i) the 2D-MMCA array; ii) the direction of DNA separation (vertical arrow); the direction of the scanning laser beam (horizontal arrow); and iv) emitted fluoresence from each capillary (cones).

In one embodiment, the present invention contemplates a two-dimensional monolith multi-capillary array 1 (2D-MMCA) as a carrier for the CE separation. See FIG. 1. In one embodiment, the array comprises fused silica. In one embodiment, the array is fabricated by a capillary pulling technique. In one embodiment, the array comprises k×l capillaries, wherein "k" ranges between approximately 25-500, preferably between approximately 50-350, and more preferably between approximately 75-125 capillaries, and wherein "l" ranges between approximately 75-1500, preferably between 150-1250, and more preferably between approximately 250-375. In one embodiment, the array comprises 100×300 capillaries. In one embodiment, the capillaries are approximately square. In one embodiment, the capillaries comprise an inner diameter of approximately 10-150 µm, preferably 25-100 µm, but more preferably 30-50 µm. In one embodiment, the capillaries comprise a pitch of approximately 20-300 µm, preferably 40-200 μm, but more preferably 60-100 μm. In one embodiment, the capillary length comprises 15-45 cm, preferably, 10-30 cm, but more preferably between 5-15 cm. In one embodiment, the capillary is filled with a separation matrix.

In one embodiment, the present invention contemplates a device comprising a 2D-MMCA, a laser source, and a multi-pixel photodetector, thereby allowing simultaneous illumination and detection of up to 30,000 CE lanes (i.e., for example, an array comprising 100×400 capillaries). In one embodiment, the laser source comprises an optical line generator. In one embodiment, the laser source operates in a scanning fashion, wherein a highly parallel thin laser beam illuminates each capillary row individually. In one embodiment, four hundred (400) rows wherein each row comprises one hundred (100) capillaries are individually (i.e., row-by-row) illuminated. Side illumination of linear capillary arrays of 100 and more capillaries and sequencing detection of multiple CE channels by scanning has been reported (e.g. sequence detection in 384 microfabricated channels with a single 100 mW Ar-ion laser). (Emrich et al., 2002). Consequently, this embodiment of the present invention provides more than a 100-fold increase in throughput when compared to both commercial and microfabricated CE systems.

In one embodiment, the present invention contemplates a method of detecting nucleotide bases. In one embodiment, the detecting comprises fluorescence excitation. In one embodiment, the detecting comprises multicolor modulation excitation and emission detection. U.S. Pat. No. 5,784,157 (herein incorporated by reference).

Although it is not necessary to understand the mechanism of an invention, it is believed that in order to create a sequencing system based on 2D-MMCA, a method of DNA preparation and amplification that conforms to the array geometry, does not require splitting capillary ends, and allows an efficient injection of individual DNA samples into individual capillaries of the 2D MMCA should be utilized. It is further believed that this approach is related to cycle array amplification technologies.

B. Gel-Based Nucleotide Amplification

Despite innovations in DNA amplification methods (e.g., strand-displacement amplification (Walker et al., 1992; Westin et al., 2000), rolling-circle amplification (Lizardi et al., 1998), PCR still remains the most utilized one due to its efficiency and versatility. Progress in miniaturization of PCR volume, reported as limited to ~100 picoliters because of reaction chemistry and kinetics. (Nagai et al., 2001). However, this miniaturization progress revealed new challenges to overcome, for example: i) providing a connection to the macro world; ii) operating within sub-nanoliter vessels; controlling reactant dispensing; and iv) controlling product extraction, etc.

Development of tethered nucleic acid technologies (Gillespi & Spiegelm, 1965; Kafatos et al., 1981) into oligonucleotide microarrays (Southern et al., 1999) provided one way to overcome these "logistical" problems. But as polymerase-mediated template amplification was demonstrated on microarrays (e.g., (Maskos & Southern, 1993)), it became clear that kinetics of surface-bound PCR is about 100 times slower than that of PCR in a volume (Tillib et al., 2001) resulting in the development of gel matrix-immobilized PCR technology. One current approach to gel-based PCR technology primarily employs sets of different primers covalently bound inside individual nanoliter-scale "hydrogel" drops/pads arranged in regular microchips arrays for washing with multi-template solutions for hybridization and thermocycling amplification. (Strizhkov et al., 2000; Rubina et al., 2004).

Another current approach first combines PCR reactants, primers, and a terminally diluted template with gel monomer and then traps them in a thin polyacrylamide matrix layer (i.e., tens of μm) formed during polymerization. (Chetverina & Chetverin, 1993; Mitra & Church, 1999; Chetverina et al., 2002; Mitra et al., 2003). In this modification, thermocycling results in growth of individual colonies of single template molecules (i.e., PCR colonies, or polonies) growing to between 5 to 100 μm in diameter in a volume of approximately 0.1 pl-1 nl. This technique may be used to grow approximately $5 \times 10^6$ colonies on one slide and can be replicated repeatedly similar to replicas of bacterial colonies on agar plates. (Mitra & Church, 1999). Polonies created using this technique are not easily extractable from the gel for further manipulations, but are susceptible for follow-up sequencing reactions within the gel. Moreover, these polonies appear to be conducive for the direct sequencing of PCR products without clean-up due to immobilization of primers and their extension products on the matrix. (van den Boom et al., 1998; Hashimoto et al., 2003).

In one embodiment, the present invention contemplates a device comprising a gel- (or otherwise) immobilized PCR platform for developing a sequencing system based on 2D-MMCA. Although it is not necessary to understand the mechanism of an invention, it is believed that a gel-based 2D-MMCA nucleotide sequencing system confers a benefit by eliminating microbiological cloning procedures, and by accommodating existing protocols and diverse underlying chemistries at a high level of miniaturization and parallelism. It is further believed that the use of 2D-MMCA adds a third dimension by converting an essentially planar polony or gel microchip technology into a 3D assay.

In one embodiment, the present invention contemplates a small polony size. In one embodiment, the polony size ranges between approximately 10-30 μm. In one embodiment, the polony is split-end free. In one embodiment, the polony electrophoretic separation is diffusion-limited (i.e., as opposed to diffusion- and plug-limited as in conventional CE separations). In one embodiment, the present invention contemplates electrophoretic separation in short capillaries using short run times. In one embodiment, the capillary ranges between approximately 10-15 cm. See FIG. 2.

In one embodiment, polonies are distributed on a gel plate 4 using a printer head or spotting machine. (Blanchard et al., 1996). In one embodiment, the spotting machine distributes polonies non-stochastically. In one embodiment, the non-stocastic spotting results in polony growth at exactly addressable spots. Although it is not necessary to understand the mechanism of an invention, it is believed that a printer head or spotting machine achieves precise spotting of the sample on gel, as opposed to mixing a sample in a gel mix and then spreading the mix on a supporting substrate to gel.

In one embodiment, the present invention contemplates a device comprising electrokinetic loading of a capillary. For example, each individual capillary of the 2D-MMCA is attached to one exactly addressable spot on a gel plate and electrokinetically picks a sequencing ladder from that individual polony.

The above considerations show that the combination of gel-immobilized PCR amplification and cycle sequencing with CE separation and fluorescence detection in 2D-MMCA offers a clear and feasible way for 100-fold increase of the throughput of DNA sequencing systems and potentially enables both re-sequencing and de-novo sequencing of large size genomes.

C. Reaction Methodology

1. Template DNA Library Preparation

In one embodiment, the present invention contemplates genomic DNA isolation and fragmenting, template DNA cassette preparation, purification, quantification and dilution to the rate of ~1 template molecule per 0.1 nl using commonly used techniques.

2. Gel-Plate Preparation, PCR, and Cycle Sequencing

Existing protocols describe gel-immobilized amplification of 500-2,000 bp long DNA templates which is sufficient for the re-sequencing. (Mitra & Church, 1999; Vasiliskov 1999; Mitra et al., 2003). De-novo sequencing can be optimized using a gel-based PCR protocol to achieve an amplification of longer templates (i.e., for example, at least 3-5 kilobase pairs), since PCR in gels exhibits similar kinetics as in free solutions. The cycle sequencing extension of immobilized templates has been reported that indicates the amount of extended product was sufficient for high resolution fluorescence detection. (Soper et al., 1998; Margraf et al., 2004).

3. Capillary Electrophoresis and Fluorescence Detection

Electrokinetic injection and CE separation of the extended products has been described. (Soper et al., 1998; Margraf et al., 2004). A 2D-MMCA fabrication of fused silica (i.e., for example, a capillary array 53 for CE DNA separation does not require any additional technology development but rather careful optimization and adjustments of all system components involved in this step. For example, a DNA sequencer can be designed and implemented to achieve an efficient and robust assay for under $1,000,000 involving the coordinated efforts of engineers, molecular biologists, and computer scientists. In one embodiment, the present invention contemplates a 2D-MMCA technique providing sequencing of mammalian size genomes for $100,000. Practically all subsystems of this proposed DNA sequencing instrument significantly differ from a 96-lane DNA sequencer (infra). However, all subsystems and modules of the proposed instrument can be designed based on already existing and very well developed electronic, optical and computer components.

D. Fabrication Methods

In one embodiment, the present invention contemplates a method to produce monolith multi-capillary arrays. One method utilizes a set of glass ferrules whose number is equal to the desired number of channels. The size and the shape of the ferrules and the thickness of their walls are chosen depending on the desired inner size of the capillaries and the spacing between them. The ferrules are pressed together in a planar array and are drawn at an elevated temperature. Ferrule adhesion or fusion occurs during the drawing process results in an array having a monolithic structure.

In one embodiment, ferrule formation of regular arrays results in square or rectangular capillaries 14 comprising translational symmetry. Although it is not necessary to understand the mechanism of an invention, it is believed that a monolithic array acts as a low-loss medium for the propagation of light, consequently conferring optical properties that provide a uniform illumination on all capillaries. It is further believed that this property facilitates focusing a laser beam 2 on the center of the capillary. Significant advantages of the MMCA include their low cost and the absence of any specially adjusted parts in the detection zone. The MMCA fabrication facility has the capacity of pulling a 6-meter MMCA. The entire six-meter structure is cut to provide a plurality of smaller MMCAs having any required length. See FIG. 3.

2. Step-Wise Preparation and Analysis

The present invention contemplates specific advantages over conventional sequencing methods including, but not limited to, the elimination of sample preparation steps (i.e., for example, bacterial cloning), high level of miniaturization, massive parallelism, integration of DNA amplification, time savings, and cost savings. A brief step-by-step description illustrating some embodiments of sequencing technology contemplated by the present invention is presented below.

a. Template DNA Library Preparation

This step can be implemented using standard, commonly used techniques. For example, the techniques include, but are not limited to, genomic DNA isolation, DNA fragmenting, fragment separation, ligation of two different universal primer-binding sites to the ends of variable region (See, for example, Singer et al., 1997), and template DNA cassette purification, quantification and dilution to the rate of ~1 template molecule per 0.1 nl (i.e., for example, limiting dilution technology).

b. Gel-Plate Preparation

In one embodiment, this step prepares mirror-symmetrical pairs of glass and/or plastic plates (i.e, for example, 80 mm×96 mm) coated with an ultra thin (i.e., for example, 50-100 μm) polyacrylamide gel containing a PCR mix. See FIG. 4A and FIG. 4B. In one embodiment, for each set of DNA colonies, the paired plates are configured face-to-face, thereby covering and sealing each other.

I) PCR Gel Mix

In one embodiment, the gel mix contains reagents to support a PCR reaction mixed in with gel forming reagents. In one embodiment, these reagents include, but are not limited to, acrylamide (i.e, for example, 6-20%) and bisacrylamide (i.e, for example, 1/19 the percentage of acrylamide). (Mitra & Church, 1999; Mitra et al., 2003). Two sets of the gel mix are prepared, one for each paired plate: Plate A 17: Mix A containing up to 1 μM of primer A with an acrydite modification at its 5' end (Vasiliskov et al., 1999), and up to 1 μM of free primer B; Plate B 18: Mix B containing up to 1 μM acrydite-modified primer B and up to 1 μM free primer A.

II) Polyacrylamide Gel Plate

PCR Mix A is poured onto Plate A, and Mix B is poured onto Plate B. Plate A and Plate B are then individually covered with teflonated glass or plastic coverslip and polymerized. (Mitra & Church, 1999; Mitra et al., 2003). As a result, Plate A of each paired plate contains Primer A covalently bound to the gel associated with free Primer B. Plate B of each paired plate contains Primer B covalently bound to the gel associated with free Primer A. (Vasiliskov et al., 1999). Although it is not necessary to understand the mechanism of an invention, it is believed that a variety of chemistries are available to make nucleic acid species permanently and/or reversibly bound to a gel matrix (e.g., (Rubina et al., 2004)). After preparation, the frames with gel-plates are washed, sealed and stored at 4° C.

c. Polymerase Chain Reaction Amplification

Many protocols are available that describe amplification of 500-1,000 base pair polonies which is sufficient for re-sequencing techniques. (See, for example, Mitra & Church, 1999). De-novo sequencing, however, may require optimization of the gel-based PCR protocol to achieve amplification of longer templates (i.e., for example, 3-5 or more kilobase pairs).

I) Template Dispensing

In one embodiment, template solutions are dispensed (i.e, for example, 0.1 nl portions) using a high precision printer head (or spotting machine) and 2D-positioning stage for the precise spotting of the solution on gel plates. (Blanchard et al., 1996). In one embodiment, a 0.1 nl droplet (i.e., for example, ~Ø30 μm) of a template solution is spotted on a gel Plate A having a 100 μm pitch. In one embodiment, the spots are organized in clusters. In one embodiment, the cluster comprises 55×55 spots. In one embodiment, a plate comprises 8×12 clusters (i.e., 96 clusters). In one embodiment, a plate comprises 290,400 template spots. Although it is not necessary to understand the mechanism of an invention, it is believed that due to Poisson distribution, about 36% of the spots are empty, about 36% of the spots contain single template molecules (thereby producing a single clone polony), and the remaining approximate 28% of the spots contain two or more template molecules (thereby generating a mixture of two or more DNA polonies).

II) PCR Cycling

In one embodiment, Plate B is turned over and configured to cover and seal Plate A (i.e., for example, gel Mix A and gel Mix B face and contact each other in a sandwich between the Plate A and Plate B mounts). The sealed gel Plate A/B complex is then placed into a thermocycler and cycled 40 times to create polonies of approximately 30-50 μm in diameter. Although it is not necessary to understand the mechanism of an invention, it is believed that since polony size is inversely proportional to the template length and the gel density for a given template, acrylamide concentration can be adjusted to keep DNA colony to obtain any desired dimension. (Mitra & Church, 1999).

d. Cycle Sequencing

I) Washout

After completion of the PCR cycling, the sealed gel Plate A/B complex is opened and the respective gels are separated. Each gel now contains the DNA colonies that are mirror-image replicas of its paired gel. Each Plate is then washed out in a manner similar to a denaturing step. Plate A then comprises A-primed single DNA strands linked to the gel by their 5' ends. Plate B then comprises complementary B-primed single DNA strands are linked to the gel by their 5' ends. Mitra et al., (2003)

II) Extension Reactions

In one embodiment, a sequencing reaction mix (i.e., for example, Big Dye®) is poured on each gel Plate. In one embodiment, the sequencing reaction mix for Plate A comprises sequencing primer B. In one embodiment, the sequencing reaction mix for Plate B comprises sequencing primer. The sequencing primers are added in excess. Although it is not necessary to understand the mechanism of an invention, it is believed that this reduces the role of free primers from the contralateral gel, to win competition for the polymerase. (Hashimoto et al., 2003).

The separated gel plates are then covered with a teflonated coverslip, and thermocycled 10 times. After the cycle sequencing is completed, the plates are opened, washed and a denaturing buffer is added. Plate A now comprises free B-primed dye-terminated sense sequencing products and bound A primed dye-terminated antisense sequencing products, as well as PCR products (i.e., for example, bound A-primed antisense strands and free B-primed sense strands). Plate B now comprises free A-primed dye terminated antisense sequencing products and bound B-primed dye-terminated sense sequencing products, as well as PCR products (bound B-primed sense strands and free A-primed antisense strands). (See FIG. 4, arrows indicate pairs of forward and reverse extended polonies).

One advantage of the above embodiment is that both sense sequencing products (i.e, for example, Plate A) and antisense sequencing products (i.e, for example, Plate B) can be generated in direct sequencing of polonies without or with minimal polony clean-up. Bound primers have been reported previously to generate sense and antisense sequence information in standard PCR/CE configurations. (van den Boom et al., 1998; and Hashimoto et al., 2003). Polony tracking software allows linking the separate reads from Plate A and Plate B to be arranged in read pairs for further use in the sequencing assembly (infra).

e. Capillary Electrophoresis

I) Re-Sequencing

In one embodiment, re-sequencing very small polonies (i.e., for example, <10-40 μm) is performed utilizing diffusion limited separation. In one embodiment, a 10-12 cm capillary provides an electrophoretic separation with an approximate 400 base pair read length. Although it is not necessary to understand the mechanism of an invention, it is believed that this embodiment allows a DNA Sequencer to operate in the most economical fashion providing the minimum sequencing cost.

II) De Novo Sequencing

In one embodiment, de novo sequencing comprises 30-35 cm capillaries providing electrophoretic separation with an approximate 800 base pair read length. Although it is not necessary to understand the mechanism of an invention, it is believed that increased sample run time, decreased throughput, and increased sequencing cost in this embodiment can be offset by utilizing a sample tracking system to obtain read pair links.

III) Electrokinetic Injection of Polonies into 2D-MMCA

In one embodiment, the present invention contemplates a CE unit wherein an inlet end of a 2D-MMCA is directly attached to the gel plate 4. In one embodiment, an individual capillary opening is placed directly above an individual spotted polony. In one embodiment, a single 2D-MMCA 1 covers a group of 48×64 spotted polonies. In one embodiment, an injection voltage is applied between an addressable contact pad under a group of 48×64 spotted polonies and the top of a 2D-MMCA, wherein the array is attached to a buffer reservoir. After the electrokinetic injection is done, the inlet end of the 2D-MMCA 1 is placed into a buffer reservoir 5 to run CE separation. See FIG. 1 and FIG. 2.

IV) CE Separation

In one embodiment, the present invention contemplates a capillary electrophoretic separation method comprising a 150-200 V/cm electric field applied for an appropriate time. After the completion the run, the 2D-MMCA is placed over the next cluster of polonies and the injection and CE steps are repeated with all 96 polonies' clusters.

V) Detection of Fluorescently Labeled DNA Fragments

In one embodiment, the present invention contemplates a method to detect fluoresence using a highly sensitive cooled CCD of linear arrays of single photon detectors. In one embodiment, the detected sequencing traces are recorded by a computer and processed to produce data (i.e. traces obtained from capillaries which carry "pure" product of amplification and extension of single DNA fragments (~36% of capillaries pick dye-terminated fragments of single clones).

VI) Washout and Storage

If desired, the gel plate pair is washed, filled with storing buffer solution, sealed, and stored frozen for further colony tracking and cloning.

E. Custom DNA Sequencers

1. A 32 Lane DNA Sequencer

In one embodiment, the present invention contemplates the design and/or redesign of DNA sequencer to accommodate the specific requirements of top surface fluorescence detection using CE. For example, a 32-lane DNA sequencer 26 may be based on single photon detection 34 that is configured in three-dimensions (i.e., 3D). See FIG. 7 Panels A & B. In one embodiment, the sequencer footprint is approximately 50×25×22 inches. In one embodiment, the sequencer modules are positioned in two levels. In one embodiment, the level comprises a base level 27 including, but not limited to, an automated sample loading system 30, the programmable high voltage supply 35, the dc power supply 63, the fiberized Ar-ion laser 32, the temperature controller 29, the automated syringe 66 for polymer refilling, and onboard computer PC-104 (SERVER) 36 with a slave card. In one embodiment, the level comprises an upper level 28 including but not limited to, an optical system 31, the automated polymer block 37, and the array heating system 29.

In some embodiments, the sequencer system comprises at least two miniature blocks connected through Peek® tubing, a polymer reservoir 45, a buffer reservoir 57, at least one syringe 66, at least one syringe filling valve 44, and at least one syringe actuator 46. See FIG. 8A. In one embodiment, the system further comprises a buffer block 42, 43, 57 connected to an outlet of the capillary array 53, wherein the buffer reservoir 57 serves for filling of the capillary array with the polymer. See FIG. 8B. In one embodiment, the system further comprises a syringe block holding a polymer reservoir 45 that serves to refill the syringe 66 with fresh polymer. See FIG. 8C.

2. 2D-MMCA DNA Sequencers

In one embodiment, the present invention contemplates adding one degree of freedom to injection and detection of DNA samples which undergo CE separation using a 2D-MMCA technique. In one embodiment, a 2D-MMCA provides a two order of magnitude increase in throughput for CE-based DNA sequencers.

Although it is not necessary to understand the mechanism of an invention, it is believed that the two-dimensional topology of the 2D-MMCA's detection area directs the design of the fluorescence excitation and detection system. For example, one efficient sequence detection technique is based on simultaneous side illumination of an entire capillary array and detection of all capillaries with CCD sensors using diffraction grating for color decomposition (ABI Prism instruments) can not be applied for 2D-MMCA since it would simultaneously use the entire surface of the CCD sensor for detecting just one row of the 2D-MMCA. Another option could be to use highly sensitive 2D array of photosensitive detector (e.g. CCD sensor, of matrix of photodiodes) in conjunction with either, sequential channel illumination in scanning fashion or simultaneous illumination using cylindrical optics (e.g., an optical line generator). However, when using a color detection system (e.g. filter wheel) this approach for 2D-MMCA becomes problematic since all channels need to "see" the same filter during one frame of the detector or one scan of the illumination system.

In one embodiment, the present invention contemplates a synchronous fiberized illumination/collection/detection system 6,7 based on scanning the 2D-MMCA 1 with a laser beam 2 and receiving the fluorescence 3 by linear multi-pixel photodetectors 7. See FIG. 2.

In one embodiment, the 2D-MMCA sequencer comprises a footprint of approximately 18×11×18 inches, wherein a plurality of modules are positioned on two levels. In one embodiment, a base level 27 comprises an automated sample injection system, a programmable high voltage power supply 60, a DC power supply 63, a temperature controller 62, an automated polymer replacement unit 59, an on-board computer PC-104 (SERVER) 36, and a master control board 61. In one embodiment, an upper level 28 comprises a fiberized laser focusing system 49, a scanning assembly comprising an illuminator, a collector, and a detector, an automated polymer replacement block, and an array heating system 55. In one embodiment, the sequencer further comprises an external computer (CLIENT) comprising controls for operations including, but not limited to, instrument operation, data visualization, data recording, data transfer, and a technician interface terminal. See FIG. 9.

3. Polymer Replacement Modules

In one embodiment, the present invention contemplates a sequencing method comprising spotting DNA samples on a gel-plate in such a way that when a 2D-MMCA is applied to the sample tray, the sample's spots are aligned with the array's capillaries. In one embodiment, the sample tray comprises DNA material for 96 injections. In one embodiment, an electrokinetic injection at an inlet end of a m×n 2D-MMCA covers m×n sample spots. In one embodiment, the outlet end of the MMCA is inserted into a transparent polymer replacement block. In one embodiment, an applied injection voltage injects a DNA product from the gel plate into an MMCA capillary. Although it is not necessary to understand the mechanism of an invention, it is believed that in order to prevent drying of the gel plate between injections during the separation time, the precision sample stage moves the sample plate to the plate cover, simultaneously, the inlet end of the array is immersed into buffer reservoir for running the CE separation.

In one embodiment, the present invention contemplates a polymer replacement module B59 wherein an injected DNA fragment moves from a gel plate 54 towards the 2D-MMCA 1 outlet, under conditions such that the fragments reach the array's outlet and are illuminated by a scanning laser beam 2 (i.e., but still inside of the array's capillaries). See FIG. 10. One main advantage of this design is that it enables fluorescence detection from the top of the 2D-MMCA. In one embodiment, the present invention contemplates a method comprising; i) installing a 2D-MMCA 1 and tightly fixing the array in a precision fixture on the lower polymer block 64; ii) inserting a syringe 66 in the upper polymer block thereby loading the syringe with polymer from the polymer reservoir; closing the upper block valve 67 and opening the lower block valve 68, wherein by pumping the syringe 66 the lower block 64 is filled with polymer. In one embodiment, the lower block valve 68 may be configured to either fill an array 1 with polymer (i.e., with the valve closed), or remove air bubbles (i.e., with the valve open). In some embodiments, the system is automated wherein both valves and the syringe are operated by computer controlled linear actuators. In one embodiment, the method further comprises scanning the capillary array rows with the laser beam along an X axis close to the top surface of the polymer block, thereby resulting in a fluorescence image. In one embodiment, the fluorescence image 3 is collected by a fiberized collection lens 48 (i.e., for example, a Relay® lens) and delivered to a rotating filter wheel 95 by fiber collectors 71 for detection by a single photon detector module 58. In some embodiments, a polymer replacement module 59 allows loading of POP-7 and IPN-60 polymers into approximately 3,000 to 30,000 lanes at a rate of approximately 50 μl/hour per capillary. In one embodiment, a polymer replacement module enables precision positioning (i.e., for example, ±10 μm). In one embodiment, a polymer replacement module enables uniform illumination of all capillaries (i.e., for example, approximately 80%). In one embodiment, a polymer replacement module enables efficient fluorescence detection from the top surface of a 2D-MMCA (i.e., for example, greater than 50%).

Although it is not necessary to understand the mechanism of an invention, it is believed that the laser beam scans the MMCA's rows very close to the top of the array. Consequently, in some embodiments, the fluorescence of the labeled DNA fragments is collected by the scanning fiberized collection lens 74 from the top of the array and via fiber collectors 71 delivered to the rotating filter wheel 95. In one embodiment, the filter wheel has up to four (4) radial slots corresponding to four (4) band pass filters, wherein each slot has a fiber adapter and can accommodate up to 32 fiber-collectors terminated with collimating GRIN lenses 81. In one embodiment, an array of fiber-collectors 73 is split into four bundles, wherein each bundle is connected to a separate filter slot.

In one embodiment, the collimated fluorescence signal passes through the filter wheel 95 and individual fiber collectors 71 where the signal is delivered as individual pixels to a multi-channel single photon detector 58. In one embodiment, a detector comprises a 32-channel PMT (Hamamatsu). In one embodiment, a detector comprises a fiberized APD detector. After detection, the signal is transmitted to a multi-channel fast photon counter and further to a computer where it is recorded and processed.

4. Scanning Fiberized Fluorescence Systems

In one embodiment, the present invention contemplates a system comprising a 2D-MMCA 1 fixed in the transparent polymer replacement block 59, a laser beam focusing module 49, a scanning mirror 50 which enables sequential illumination of rows of the array's capillaries, and a fiberized fluorescence collection lens 74 which scans along the array synchronously with the mirror and collects fluorescence from the top of the array through the transparent wall of the polymer block. See FIG. 11.

In one embodiment, the synchronization between a mirror and a fiberized lens is provided by a precision camshaft mechanism 76 by using identical cams, and therefore having the same motion profile for the mirror and the lens (the camshaft mechanism and its driver 72 can be assembled from commercially available parts).

In one embodiment, the present invention contemplates a method for synchronization between revolutions of the filter wheel and the scanning illumination detection system. Although it is not necessary to understand the mechanism of an invention, it is believed that this synchronization ensures that the assembly of collection fibers coupled to the lens is always aligned with the image of the illuminated capillary row. In one embodiment, the fiber assembly comprises processed fiber tips to provide high (up to 50%) fluorescence collection efficiency. In one embodiment, the collected fluorescence is delivered by the fibers to a rotating filter wheel. In one embodiment, each filter wheel can pass fluorescence from thirty-two (32) individual collection fibers and discretely transfer them to a single photon detector.

In one embodiment, the present invention contemplates a multi-lane fiberized fluorescence delivery system comprising a 4-color fiberized 32-lane filter wheel with encoded filter. See FIG. 12. Although it is not necessary to understand the mechanism of an invention, it is believed that the number of channels in the system is selected based on the number channels of the single photon photomultiplier tube, as well as a single photon APD detector with synchronous quenching circuit. In one embodiment, a 32-lane array of multi-mode fibers 71 (i.e., for example, 62 μm core and 120 μm cladding, FC/PC connectorized 83) is coupled to the array of ¼ wavelength, 1 mm GRIN lenses 81, NSG, NJ, using glass ferrules 82. It is further believed that the collimated light from the fibers goes through the filter wheel in such a way that all fibers "see" the same filter, such that after the filtering, the collimated fluorescence can be either directly detected by the 32-channel PNT or again collected by the fiber assembly (75% collection efficiency) and transferred to fiberized APD detector.

In one embodiment, the present invention contemplates a mutliplex filter wheel comprising the coupling of up to four 32-lane single photon detectors (i.e., 128 lanes). In one embodiment, the multiplex fiber assembly is easily plugged into the output of the wheel for easy replacement of the standard 32-channel photomultiplier tube. Therefore in order to install an APD based photodetector, the individual fibers of the assembly can be directed connected to individual APD detectors.

5. Synchronization Systems

In one embodiment, the present invention contemplates an illumination/collection system based upon scanning rows of 2D-MMCA by a laser beam. See FIG. 13. Although it is not necessary to understand the mechanism of an invention, it is believed that the synchronization of the scanning system with the rotating filter wheel directly supports the sequencer's operation. In one embodiment, 5-10 four-color data points are received per sec corresponding to 5-10 revolutions of a filter wheel. Consequently, the scanning system must pass all rows of the MMCA during the time interval corresponding to the passage of one filter (~¼th of the revolution period). Thus, the scanner must perform 20-40 passages in 1 second. For example, if the number of capillary rows in the MMCA is 316, than each capillary "sees" the laser beam for only 1/316 part of the passage time (more accurately, it is necessary also to take into account the ratio of the capillary diameter to the array pitch). In one embodiment, the synchronizing of 316 rows results in a lane observation time of approximately 160 μs per scan. Although it is not necessary to understand the mechanism of an invention, it is believed that any fluorescence detection and recording system must be very fast in order not to loose photocounts, however, the dynamic range of single photon detectors contemplated by the present invention are sufficient for receiving such signals. In one embodiment, the synchronization signal comes from the filter wheel and controls motion of the scanning module.

6. Electrokinetic Sample Injection Systems

The electrokinetic sample injection system can be mounted on a precision 3D stage. (See FIG. 9). Although it is not necessary to understand the mechanism of an invention, it is believed that the 3D stage is advantageous by allowing a very accurate alignment of the 2D-MMCA and subnanoliter DNA samples spotted with micrometer precision on the sample plate.

In one embodiment, the present invention contemplates a gel pad slide 54 (i.e., for example, a plastic board) comprising a gel pad array 103, wherein a 2D-MMCA 1 is positioned above at least a portion of the array, thereby facilitating an electrokinetic injection. In one embodiment, the gel pad slide comprises an 8×12 gel pad array. (See FIG. 14A) In one embodiment, a plurality of array contact pads 84 are positioned on the top surface of the slide 54. (See FIG. 14B). In one embodiment, the contact pins 87, 89 on the slide are distributed on the bottom surface of slide 54. (See FIG. 14C). In one embodiment, the contact pins are arranged in the standard order for socket connection. In one embodiment, the contact pins are distributed on the top and bottom surface of the slide, thereby conferring an advantage of minimizing plate size. In one embodiment, the plate design is configured for individual addressing of injection zones, which can also be used for denaturing of individual injection zones before injection. In one embodiment, the present invention contemplates a method comprising denaturing using an array of Peltier heater/coolers 55 on the sample stage configured beneath the sample plate. Although it is not necessary to understand the mechanism of an invention, it is believed that individual addressing of injection zones is very important since with an appropriate ratio of the capillary diameter-to-array pitch it allows a "carry-over free" injection. (See FIG. 14C and FIG. 14D).

7. Computer Control Systems

In one embodiment, the present invention contemplates a computer controlled data acquisition, management, and tracking system. In one embodiment, the computer system comprises:

i) a DNA Sequencing Unit comprising: a) a DNA sequencer; b) a DNA Computer, wherein the computer in control of the DNA Sequencer, said computer comprising a FireWire® 800 link to support primary data acquisition, a Gigabit Ethernet controller to transfer data to the DNA NAS units (Est. Cost. $2000); c) a DNA NAS, N comprising a Gigabit Ethernet enabled Network Attached Storage that caches the acquired data by the DNA Computer, until it is processed by the DCPs; as the rate of data retrieval by the DCPs is limited due to cost considerations, several NASes are used by the DNA computer in a round-robin fashion. (Est. Cost. $1000 per unit); and d) a Gigabit Switch comprising a base 1000T 8-port switch to support the data exchange in the DNA Sequencing Unit. (Est. Cost. $300)

ii) a rack of DCP computers comprising a number of DCP computers needed to analyze the acquired data in real-time. As a single DNA Sequencing Unit has the capability to acquire up to 80 samples a second, this configuration can reduce the processing time of a single sample to one second, consequently, the rack contains on the order of 100 DCPs per DNA Sequencing unit. (Est. Cost. $600 per DCP, $60000 per DNA Sequencing Unit)

iii) a manager computer comprising a standard PC that works in the role of the Manager Computer. (Est. Cost. $1000);

iv) a database comprising a server-grade PC that hosts the DNA, User, and Request databases. (Est. Cost. $3000)

v) a databank N. comprising several independent computers to store different acquired samples. The optimal configuration depends on the amount of DNA Sequencing Units, the data retention time, and other factors. This arrangement overcomes the current unfeasability to have a single cheap data storage system that can handle computers to store different acquired samples. (Est. Cost for permanent retention $1 per 5000 samples, as a sample can be stored in 200 kB).

vi) a webserver hosting the customer webserver. (Est. Cost. $1000-$5000 depending on number of users.)

vii) a switch (i.e., for example, 1000T, 64+ ports) having the capability to handle all the DCPs and Databank Computers connected to it. (Est. Cost. $10000 per DNA Sequencing Unit)

In one embodiment, the present invention contemplates a computer system workflow comprising a customer of the sequencing facility receiving a tray registration number and filing an order for processing of a sample tray by filling out an on-line form by accessing the web site of the sequencing center. In one embodiment, the form provides all information necessary for running and processing the submitted material. A supplementary description of the samples can also be provided by the customer for his/her own convenience.

In one embodiment, an order registration is completed by creating a new record in the Request Database, wherein the Request Database automatically generates the folder and trace names. Although it is not necessary to understand the mechanism of an invention, it is believed that in order to provide a compatibility with the CSHL quality tracking software, the folder contains a configuration file with the name of the DNA Computer, the date of the run, the run number; the trace name contains the plate name, the plate address, and the type of sequencing reaction. After registration, the sample tray is sent to the sequencing facility for processing. An operator at the sequencing center receives the tray and inserts it into the next available sequencing machine. The tray registration number is entered manually using a keypad. The DNA Computer sends notification about the new tray installation along with its registration number to the Request Database. If the corresponding record is found in the database, the DNA Computer is allowed to start the sequencing of the sample tray.

Following sequencing initiation, the entire set of operations with DNA samples and the resulting sequencing data is performed automatically, completely without human intervention. The processing results along with the raw data and the accompanying user provided information are recorded to the DNA Database. The customer is notified about the results of the processing by e-mail or other electronic means, if so requested in the request form. The DNA Computer controls the DNA Sequencer by sending commands that specify the actions necessary for the execution of all phases of the series of runs required for running each sample on the tray. The DNA Computer also performs the acquiring and preprocessing of the sequencing data acquired and sent by the DNA Sequencer.

This data is then sent to a DNA NAS unit that is currently unoccupied. A new complete raw data file is produced by the DNA Computer at the end of each sequencing run. The Manager Computer is constantly scanning all DNA NAS units, detecting complete raw data files. Once a new complete raw data file is detected, its name, as well as the name of the DNA NAS unit which holds the file, is placed in the queue of unprocessed files. The Manager Computer dispatches the processing of the files from this queue to any available Data Processor. The file name is moved to a 'in progress' list once the processing of the file is started, and to a 'finished' list upon the completion of processing. Once the processing is finished, processing results, raw data and any user provided information is stored in the DNA Database. Once the sequencing of the tray is finished and the processing results are recorded to the database, the Customer Web Server updates the Databank and the Database notifies the customer about the completion of the process.

8. Computer Control System Software

In one embodiment, the present invention contemplates a method of DNA sequencer automation based upon the control of all instrument's modules by a single board computer PC-104 (i.e., for example, SEQUENCER). In one embodiment, this computer comprises a PENTIUM-3 processor, a 256 MB cash memory and a 10 GB hard disk, interconnected by a plurality of serial and parallel ports, and a network card.

In one embodiment, all automated modules are connected to a DNA Computer (i.e., for example, the computer SEQUENCER) using a novel PC board (i.e., for example, a PC-104 slave card). In one embodiment, the PC-104 SEQUENCER comprises a software program, wherein the software controls calibration, programming and automation of all system modules including, but not limited to, a high voltage supply, a temperature controller, a plurality of thermo-sensors, a polymer replacement system, an electrokinetic sample injection system, and an instrument status display. In one embodiment, the novel software also supports a transfer of the sequencing data from the computer SEQUENCER to the computer CONTROLLER using standard Ethernet protocol.

9. PHRED Base Software

In one embodiment, the present invention contemplates a novel software enabling the use of the PHRED base—for the SB sequencer. In one embodiment, a base calling software targets a 1 second processing time per read. The raw data file obtained from the sequencer are first preprocessed to produce a set of SCF files satisfying the requirements for the input data for PHRED. A separate SCF file is produced for each sequencing lane. The created set of SCF files is processed by PHRED. The detailed information about the detected bases including their quality factors and positions is obtained from the PHRED files, which represent standard PHRED output. In order to evaluate the applicability of a PHRED quality score table to sequencing data a string analysis software is used to allow a comparison of base calling results for two sequences. The string analysis software compares theoretically predicted probability of base-calling error in a set of bases that were assigned quality factor in a selected range to experimentally observed probability of an error. The evaluation experiment requires substantial number of successful sequencing runs. The runs are performed using a DNA sample with a known sequence. The results of base-calling of the runs, represented as files containing sequences of base/quality factor pairs produces by PHRED and a file with the known sequence are presented to the evaluation software. Each experimental sequence is aligned with the 'original' precisely known sequence. The alignment is performed using Levinstein algorithm. Evaluation of the probability of incorrect calls in comparison with the probability predicted by PHRED can be determined experimentally.

F. Addressable PCR Colony Cassettes

In one embodiment, the present invention contemplates a technology platform comprising a standardized frame and/or cassette compatible with gel-plates having electrodes on the cassette's bottom underneath the gels. Although it is not necessary to understand the mechanism of an invention, it is believed that these frames and/or cassettes transform current stochastic polony technology into precise and addressable arrays.

1. Cassette Construction

In one embodiment, polony addressability comprises enclosing a thin gel into a rigid cassettes, wherein the gel carries reference points. In one embodiment, the reference points enable the integration of an polony spotting technique employing a spotting machine and MMCA-mediated sequencing reading with a high degree of precision. In one embodiment, the electrodes are addressably wired for each of 8×12=96 polony cluster arrays. In one embodiment, a single electrode accommodates a 48×64=3072 polony array. In one embodiment, each polony maintains a 3 mm spacing distance, such that 96 (5×7 mm) electrodes underlie 96 (8×10 mm) zones within an (8×12) by (10×8)=(96×80) mm gel. In one embodiment, the electrodes are made using a non-corrosive metal film deposition on a glass or plastic substrate, and pre-manufactured or re-assembled into frames/cassettes. Alternatively, custom cassettes may be machined using simplified temporary frames. In one embodiment, a temporary frame comprises a line of five (5) electrodes made of ultra thin foil attached to a glass or plastic substrate and wired. Although it is not necessary to understand the mechanism of an invention, it is believed that temporary frames/cassettes can provide experimental constructs to assess components and/or alternative steps of the technology including, but not limited to, —casting gels of various concentrations, the compositions, and chemistries; —polony spotting with DNA of different lengths, with or without some components of PCR mix; —develop and test our own template cassettes and primers; —study growth of clones of spotted DNA (width, depth, diffusion, failures, etc.)—parametric study and optimization of PCR to achieve high efficiency for ~1-3-5-10 kbp templates with highest product concentration at smallest number of steps; —study and optimize the Sanger sequencing reaction of gel-immobilized amplicons; —study, characterize and optimise the electrokinesis of ssDNA fragments (from Big Die Standard kit or in gel Sanger reaction) on the gel when current is applied between a single capillary above and a flat electrode beneath several neighboring polonies; —study, characterize and optimise the electrophoresis of ssDNA fragments using a single capillary and a linear MMCA (need for injection, parameters of injection and run, separation times and length with different media, and fluorescent signal amplitude; —further define the protocol to achieve the highest signal with a simpler procedure, especially investigate need and degree of washout steps, and streamline all the protocol in order to attain the highest signal with no or minimal sample clean-up; —finally, procedures for washing and storing of gel cassettes with clones, as well as re-amplification and re-sequencing of stored clones.

2. Template and Primer Preparation

DNA amplification cassettes are made with standard, commonly used techniques. This step includes genomic DNA isolation, DNA fragmenting, fragment reparation, ligation of two different universal primer-binding sites to the ends of variable region (Singer et al., 1997), template DNA cassette purification, quantification and dilution to the rate of ~1 template molecule per 0.1 nl.

DETAILED DESCRIPTION OF THE PREFERRED EMBODIMENTS

I. Fabrication of a Two-Dimensional Multi-Capillary Arrays

In one embodiment, the present invention contemplates a two dimensional (2D) monolith multi-capillary array (2D MMCA) which overcomes the 96 capillary limitation of previously fabricated 2D capillary arrays. In one embodiment, a 2D MMCA 1 comprises a 32×24-capillary array 53 (i.e., for example, containing 768 individual capillaries). In one embodiment, the capillaries 14 are approximately 50 mm square. In one embodiment, the array has an approximate 100 mm pitch. In one embodiment, the capillaries are approximately 10-20 cm in length. See FIG. 16.

In one embodiment, an MMCA rectangular array contour may be irregularly shaped. For example, a peripheral capillaries can be misaligned by ~100 mm. See FIG. 16, Inset 2. Although it is not necessary to understand the mechanism of an invention, it is believed that array contour misalignment can be eliminated by optimizing the array pulling regime. Fabrication of 32×24-capillary MMCAs show that further increases of the array size is feasible within the framework of the existing array pulling technique, but may require increasing the diameter of the furnace from 70 mm to 120 mm in order to improve the array uniformity.

II. Sequence Detection Feasibility in a 30,000 Capillary Array

In one embodiment, the present invention contemplates a method to determine the number of labeled DNA fragments needed for successful detection of DNA sequences in a 96×316 capillary array (i.e., for example, a total of 30,000 capillaries).

In one embodiment of a scanning, illumination, and detection method, the illumination power delivered to individual capillaries is relatively small. For example, when scanning a 96×316 capillary array along its columns, the average illumination power received by each 96-capillary column is $I_{POWER}=L_{POWER}\times1/316\times(D/P)$, where $L_{POWER}$ is the entire laser power and D/P is capillary-to-pitch ratio. See FIG. 17. In one embodiment, a 2D MMCA 1 comprises square capillaries 14, thereby providing a uniform distribution of the illumination power between individual capillaries of the column. Although it is not necessary to understand the mechanism of an invention, it is believed that individual square capillaries with a small rounding in the corners result in the illumination beam having the diameter smaller than the capillary size, thereby propagating through the 96-capillary column without significant refraction losses.

In one embodiment, a multi-lane DNA sequencer comprises an illumination beam of 20-30 μm diameter with the waist length of ~40 mm, which is smaller than the length of the 96-capillary column of the MMCA (i.e., for example, 9.6 mm) Therefore, the major loss of the illumination power is due to the beam reflection from capillary walls. Mismatch estimates of refractive indexes (RI) of the separation media (RI=1.4) and fused silica (RI=1.46) show that in 96-capillary column a refractive loss is less ~10% of the incident illumination power. Although it is not necessary to understand the mechanism of an invention, it is believed that this scanning illumination system allows practically equal illumination (i.e., for example, uniform illumination) of all individual capillaries of the 2D MMCA. Further, when using a 300 mW Ar-ion laser for illumination of the 2D MMCA with a 50 mm capillary size and a 100 mm array pitch, the illumination power per one column is $I_{POWER} \approx 0.5$ mW. Taking into account 10% reflection loss, the illumination power received by individual capillaries in the column varies between 0.5 and 0.45 mW.

The feasibility of the sequence detection was tested by carrying out a series of sequencing runs of serially diluted BigDye DNA Sequencing Standard (Applied BioSystems, CA) using 0.5 mW laser power and a single photon detection system (Alaverdian 2002). The increase of the dilution degree led to a decrease of peak amplitudes on electropherograms. A sequencing trace and Q-factor plot obtained for 1:100 diluted sample is presented. See FIGS. 18 and 19, respectively.

These results suggest that a detection system contemplated by the present invention provides a 450-600 base pair Q20 read length when peak amplitude was higher than 1250 photocounts per second.

In order to determine the number of labeled DNA fragments in one peak which would provide the peak amplitude of 1250 photocounts per second at 0.5 mW illumination power, a detection system calibration was performed using serial dilutions of fluorescein in TSR buffer (Applied BioSystems, CA). The results demonstrated that one molecule of fluorescein gave ~20 photocounts/s per 1 mW of illumination power. Taking into account the width of the illumination beam (i.e., for example, 20 mm) a linear concentration h of labeled DNA fragments along the capillary length in the peak maximum $$\eta = \left(\frac{2500 \ c/(s \times mW)}{20 \ c/(s \times mW)}\right) 20 \ \mu m = 6.25 \ \mu m^{-1}$$

may be calculated.

Further, assuming that the peaks have a Gaussian shape, and diffusion limited separation is present, the total amount of DNA fragments in the peak of amplitude h is: $N = \eta \times \sqrt{4\pi D_n t}$ where $D_n$ is diffusion coefficient, t is a sample run time, and n is Q20 read length. These calculations provide $N \approx 2100$ for POP-7 polymer when n=500, $D_{500}=6.5 \times 10^{-6}$ mm²/s, and t=1350 seconds. Therefore, the minimum total number of injected DNA fragments needed for a 500 base pair read length should be: $N \times n \approx 1,000,000$.

The number of amplified fragments in a single polony has been estimated at $10^8$ (Mitra, R. D. & Church, G. M., *Nucleic Acids Res.* 27, e34, 1999). Consequently, the injection of more than 1% of this amount is sufficient to detect sequences of 500 base pairs. Consequently, it is feasible for the embodiments contemplated by the present invention to detect and read DNA fragments of 500 base pairs.

III. Electrokinetic Injection DNA Sequencer

The present invention contemplates an injection technique called field flow injection (i.e., for example, electrokinetic injection). This technique can inject (i.e., transfer) DNA samples from a gel micro-pad 93 into a capillary array 53 (i.e., for example, a 2D-MMCA) without physical contact between the gel pad 93 and the capillary. Computer simulations have shown that injection efficiency depends on electric field, distance between the capillary and the surface of the gel slide, and alignment of the gel micro-pad with the capillary inlet.

In one embodiment, the present invention contemplates a device comprising an electrokinetic injection system, wherein a DNA extension product is directly transferred from a gel plate into a fused silica capillary. In one embodiment, the DNA extension product is separated by capillary electrophoresis. In one embodiment, the electrokinetic injector system 91 is configured with a single lane DNA sequencer.

In one embodiment, a single lane DNA sequencer is configured with an electrokinetic injection system such that a DNA extension product is transferred directly from slides comprising micro-gel pads into a single capillary. In some embodiments, DNA separation is accomplished in capillaries having various lengths (i.e., for example, between approximately 5-20 cm) at temperatures in the range of 23-70° C. controlled with precision of ±0.1° C.

In one embodiment, a DNA sequencer comprising an electrokinetic injection system 91 further comprises a polymer replacement system 59. See FIG. 20A. In one embodiment, a DNA sequencer comprising an electrokinetic injection system further comprises an optical head 31. In one embodiment, an improved optical head provides an approximate 5-fold improvement in the collection of fluorescence emitted from the capillary. See FIG. 20B. In one embodiment, a DNA sequencer comprising an electrokinetic injection system further comprises a gel slide 93 and 3D positioning system 92. See FIG. 20C. In one embodiment, a DNA sequencer comprising an electrokinetic injection system further comprises a photon counter 92 and a filter wheel system 95. See FIG. 20D.

In most embodiments, a standard electrokinetic injection field flow is applied. See FIG. 21B. Alternative field flow configurations are also contemplated by other embodiments of the present invention. In one embodiment, the present invention contemplates a field flow generated by a single (i.e., for example, isolated) capillary configuration. See FIG. 27A. Although it is not necessary to understand the mechanism of an invention, it is believed that this configuration has a greater degree of electrical protection, and therefore safer for the operators. It is also believe that a self-compressed field configuration results in a reduced divergence and a more uniform electric field distribution. It is further believed that a self-compressed field configuration results in reduced injection plug broadening. In one embodiment, the present invention contemplates a field flow generated by a single capillary surrounded by walls (i.e, for example, glass walls). See FIG. 27B. In one embodiment, the present invention contemplates a field flow generated by a capillary array positioned (i.e., at a distance above (i.e., for example, 100 μm) a conducting surface under a negative potential. See FIG. 27C.

Although it is not necessary to understand the mechanism of an invention, it is believed that a DNA sequencer comprising an electrokinetic injection system enables a very accurate 3D positioning of the gel slides with 5 mm precision. It is further believed that such precision is necessary in order to control a distribution of the electric field which is applied to gel pads during the electrokinetic injection. For example, the electrokinetic injection system simultaneously allows injection of DNA samples from a tube which is used for control runs.

IV. Gel Pad Isolation

In one embodiment, the present invention contemplates the isolation of a polymerase chain reaction amplification product and/or other sequencing product prior to the separation and sequencing steps. Previously reported are methods using polymerase chain reaction oils. Sergei et al., "Integration of Multiple PCR Amplifications and DNA Mutation Analysis by Using Oligonucleotide Microchip" *Anal Biochem* 292:155-160 (2001). This technique has many disadvantages that the present invention overcomes. In particular, various embodiments of the present invention contemplate the isolation of these products on individual gel pads.

A. High Porosity Gel Pad/Low Porosity Gel Matrix

In one embodiment, the present invention contemplates a method for isolating and polymerase chain reaction amplification and/or other sequencing product comprising placing a high porosity gel pad 97 on a low porosity gel matrix 98. See FIG. 25A. In one embodiment, a high porosity gel pad (i.e., for example, an active gel pad) comprises polymerase chain reaction primers tethered to a substrate and/or polymerase chain reaction amplification and/or other sequencing products. In one embodiment, the substrate surface in coated with a conducting coating 99. Although it is not necessary to understand the mechanism of an invention, it is believed that a very slow DNA diffusion rate in the low-porosity matrix prevents the DNA products present in the individual high-porosity gel pad to penetrate into other (neighboring) high-porosity gel pads. In one embodiment, the electrokinetic voltage is applied between a conducting coating (−), said coating applied to the surface of an insulating slide substrate 100 (i.e., for example, glass, silicone, quartz, plastic etc.) and the individual gel pads (+). See FIG. 25B. In one embodiment, the conducting coating compounds include, but are not limited to, $In_2O_3$ or aluminum.

B. High Porosity Gel Pad/Pad Well Barriers

In one embodiment, the present invention contemplates a method for isolating and polymerase chain reaction amplification and/or other sequencing product comprising placing a high porosity gel pad 97 in a pad well with barriers 101 formed on the slide 54 surface. See FIG. 26A. In one embodiment, a high porosity gel pad (i.e., for example, an active pad) comprises polymerase chain reaction primers and/or polymerase chain reaction amplification and/or other sequencing products. In one embodiment, the primers are tethered to a substrate surface. In one embodiment, the substrate surface in coated with a conducting coating 99. Although it is not necessary to understand the mechanism of an invention, it is believed that the well barriers prevent DNA products in the individual high-porosity gel pad to penetrate into other (neighboring) high-porosity gel pads. In one embodiment, the electrokinetic voltage is applied between a conducting coating (−), said coating applied to the surface of an insulating slide substrate 100 (i.e., for example, glass, silicone, quartz, plastic etc.) and the individual gel pads (+). See FIG. 26B. In one embodiment, the conducting coating compounds include, but are not limited to, $In_2O_3$ or aluminum.

V. Genome Sequencing Costs

Genome sequencing cost calculations generally assume that the price for the DNA sequencing machines range between approximately $300,000-$1,500,000, for a 3,000-30,000 lane machine. Consequently, the cost of the DNA machine constitutes more than 60% of the entire sequencing cost. Although it is not necessary to understand the mechanism of an invention, it is believed that the prices for the DNA sequencers used in these calculations are much higher than the actual manufacturing cost. In one embodiment, the manufacturing cost of 30,000 lane 2D-MMCA DNA Sequencer is presented below. Table I.

TABLE I

Cost breakdown for 30,000 lane 2D-MMCA DNA sequencer

| Major Instrument Components | Cost ($) |
| --- | --- |
| Mechanical systems and parts (3D-stage movers, motors with power supplies, laser beam, scanner, etc) | 18,000 |
| Optical components and systems (96-channel fiberized illumination and collection systems, filters, lenses) | 10,000 |
| Mounting and polymer refilling systems for multi-capillary | 4,000 |
| Ar-ion laser 300 mW, single mode 20,000 96-channel single photon counting photoreciver (PMT or APD based) | 20,000 |
| High voltage power supply (15 kV 150 mA) | 15,000 |
| Temperature control system (25°-70° C. with 0.1° C. accuracy) | 4,000 |
| Computers | 22,000 |
| Case | 3,000 |
| Assembly and turning | 3,000 |
| TOTAL | 119,000 |

Table I shows that the estimated manufacturing cost of a 2D-MMCA DNA Sequencer is much lower than a commercially available conventional sequencer cost.

Additional calculations for three different instrument prices (i.e., for example, $1.5M, $750K, and $350K) which exceed the estimated manufacturing cost 3-, 6-, and 12-fold, respectively, were performed. The genome sequencing cost was seen to be dependent upon the read length as calculated for a 30,000 lane DNA sequencer, having a 7-fold coverage, and using POP-7 and IPN-60 polymers as separation media. See FIG. 27. These results show that for a 30,000-lane DNA sequencer priced at less than $750K, there is a wide range of read lengths where the cost of the genome sequencing is lower than $100K for both POP-7 and IPN-600 separation polymers. Moreover, even if the array throughput is reduced by 25% due to some capillary damage, a genome can still be sequenced for approximately $100,000.

EXPERIMENTAL

Example I

Demonstration of PCR Amplification in Polonies

This example demonstrates the reliable reproduction of the "polony" method consistent with previously reported studies. Specifically, PCR amplification of gel-immobilized 500 base pair and 1,000 base pair DNA fragments (target: 1.5 efficiency in linear PCR region) and a protocol for cycle-sequenced dideoxynucleotide-terminated extension in polonies are described.

A. ddNTP-Terminated Extension Product of Cycle-Sequencing Reaction

After reliable and reproducible polony growth has been achieved, a protocol for conducting the Sanger cycle-sequencing reaction on strands of extended gel-immobilized primers (JCF-AC or A) is performed. After polony amplification and washout, the immobilized dsDNA is denatured and the unattached DNA strand is removed by incubating the plate in a 70° C. denaturing buffer (70% formamide) for 15 min and performing electrophoresis in 0.5× TBE (90 mM Tris/64.6 mM boric acid/2.5 mM EDTA, pH 8) with 42% urea for 1 h at 5-10 v/cm. Then the slides are washed 2×4 min in wash buffer (10 mM Tris-HCl, pH 7.5, 50 mM KCl, 2 mM EDTA, 0.01% Triton X-100). Annealing mix (0.25 μM sequencing primer, 0.15 M NaCl/10 mM phosphate, pH 7.4/1 mM EDTA/0.01% Triton X-100) is added over the gel. To hybridize the immobilized JCF-AC- or A-primed ssDNA to the sequencing primer (free reverse universal primer JCR-UN or B), the slides are heated at 94° C.×2 min, then at 56° C.×15 min. Unannealed excess primer is removed by immediately washing the slides 2×4 min in a wash buffer. The slides are then washed in DI H2O 3×5 min, and the excess water is removed or dried. The sequencing reaction mix (20 μL of Big Dye Terminator Sequencing Mix (Applied Biosystems) and 20 μL of PCR-grade water) is poured over the slide. The sequencing extension fragments are generated in 10-25 cycles according to ABI specifications (e.g., denaturation at 96° C. for 10 s, primer annealing at 50° C. for 10 s, extension at 60° C. for 4 min, and a final 4° C. hold). The slides are then washed in DI H2O 3×5 min, and excess water is removed or dried. A portion of slides is used to elute and purify sequencing reaction products, which then are resuspended in HiDi Formamide, denatured, and injected in a CE capillary.

B. Electrokinetic Injection

The DNA extension product is electrokinetically injected directly from the gel plates into the fused silica capillaries and capillary lengths and run times required for DNA fragments of 100-800 base long to obtain Q20 read length are determined.

The slides are covered with 40 μL of HiDi Formamide (Applied Biosystems), incubated at 95° C. for 2 min, and snap-cooled to 4° C. in a CoolSafe® block (Diversified Biotech), then warmed to room temperature for further CE from the gel. A DNA sequencer SBS-2002 can be adapted for injection of a labeled extension products directly from gel plates into single fused silica capillaries filled with POP-5 and POP-7 polymers. (Alaverdian, 2002). Using a modified SBS-2002 sequencer, a single CE capillary with an adjacent electrode is attached to the gel surface at the earlier marked site of a polony.

The extension fragments are then be injected in the capillary and the electrophoretic separation is run. Experiments are repeated to determine optimal parameters of electrophoretic injections and runs. Injection plug characterization and injection parameter optimization, in addition to gel matrix characteristics are evaluated to obtain injection plugs smaller than 100 μm in 30 μm and 50 μm ID capillaries enabling a diffusion limited electrophoretic separation. By optimizing parameters of the cycle sequencing reaction, as well as the sample injection and running conditions, a 500 bp Q20 read length for the injected samples can be demonstrated. Multiple CE runs performed at temperatures ranging between approximately 23° C.<T<60° C. in capillaries of different length and diameter, filled with POP-5, POP-7 and IPN-60 separation media determine the influence of the temperature variation (unavoidable in the MMCA due to Joule heat dissipation) on the run time and separation quality.

C. Forward and Reverse ddNTP-Terminated DNA Extension

Using templates of known sequence, mirror-symmetric polonies in face-to-face gels are grown, wherein the separate gels are used to carry out cycle sequencing of paired polonies with forward and reverse primers. The obtained linked read-pairs are detected using SBS-2002 DNA sequencer Example II Fabrication of an MMCA This example describes the manufacture of a linear 64-lane and 96-lane MMCAs with 30 μm and 50 μm square capillary cross section, wherein the characterization of MMCA illumination and fluorescence detection is performed from the array top.

A. Single-side MMCA illumination demonstrating an approximate 80% transmission of the laser beam through the MMCA using fluorescent detection from the top of the MMCA.

Using the capillary drawing facility at SUNY Sensor CAT a borosilicate glass 55-lane and 100-lane linear MMCAs with square 30 μm and 50 μm capillary cross section and 100 μm and 60 μm array pitch is fabricated. The arrays are filled with separation media containing fluorescent dyes and illuminated from the side. The uniformity of the array illumination is measured by detecting the distribution of fluorescence in the MMCA's capillaries. See FIG. 5.

In order to carry out measurements of fluorescence excited in the MMCA, a custom fiberized precision array reading head is used. In the mounting and alignment system for the illumination fiber a Vis-NI fiber objective lens (i.e., for example, an FC/PC/APC connector, Model 014, WT&T Inc. Canada) was used in conjuction with a microscope objective lens (i.e., for example, a 10×DIN, Edmund Industrial Optics, NJ). The illumination system allows obtaining a 10 mm beam waist and an approximate 20 μm beam diameter. The mounting and alignment system for the collection/projection lens allows a precision placement and 3D alignment relative to the array fixture. See FIG. 6.

The reading head comprises three high precision sub-systems: a precision array fixture, a mounting and alignment system for the illumination fiber, and a system for mounting and alignment of the collection/projection lens. The reading head may be redesigned to accommodate any precision array fixture in order to be used for detection of fluorescence in MMCAs. This redesigned reading head allows detection of the fluorescence in the MMCA capillaries from the top of the array, which is the preferred detection geometry. Ray tracing simulations of the laser illumination of linear MMCAs show an approximate 15% optical loss for the 20 μm laser beam having 10 mm waist, when it passed hundred square 30 μm-50 μm capillaries in the MMCA made of fused silica (refractive index n=1.46) and filled with POP-7 polymer (n=1.39). An approximate 80% transmission of the laser beam through the MMCA indicates that single side illumination of the 2D-MMCA is reliable.

Example III

Addressable Cassettes: Gel-Immobilized PCR and Sequencing Reactions

This example describes a method to perform polymerase chain reaction amplification and sequencing on addressable cassettes compatible with 2D-MMCA. In the following steps, a Starter Kit kindly offered upon request by the Church group is used. The kit includes 800 bp linear template dsDNA (pCR2-1-TABS3-D5), Acrydite-modified forward primer (JCF-AC), free reverse primer (JCR-UN), Cy3-labeled sequencing primer, as well as the gel slides ready for PCR and slides on which PCR has been already conducted. The kit is used for comparing with and controlling the progress in developing our optimized protocol.

A. Casting the Gel

Casting the gel in the cassettes is done first with the following general protocol:

1. Frames with thin 5×7 mm electrodes (i.e., for example, aluminum, gold, etc) attached to glass or acrylic plastic substrate are pre-treated with Bind Silane by incubating them ~1 h in a coating solution (220 µl Acetic Acid, 4 ml Bind Silane (Amersham Biosciences), and 1 L dH20), then rinsed and dried. Alternatively, acrylated glass (CEL Associates) is used as a substrate. The teflon film frame/spacer is placed around the perimeter (50-100 µm thick) to control the gel's thickness.
2. Acrylamide gels are cast inside the frames on the slides, in a sterile DNAse-RNAse free PCR hood. Initial gel mix is: 200 ul sterile filtered gel-casting mix [30 ul 40% IEF Acrylamide (Amersham), 3 ul the Acrylamide/Bis (19:1; 38%:2%) (Roche), 0.67 mg DATD ((+)-N,N'-diallyltartramide) (Sigma-Aldrich), 1.33 uL 30% BSA (Sigma-Aldrich), 136.66 ul de-ionized H2O (DI H2O), 4 uL 5% TEMED (Sigma-Aldrich), 4 uL 5% Ammonium persulfate (APS) (Sigma-Aldrich), and 2 ul Acrydite-modified amplification primers A (100 uM)] is prepared fresh.
3. The gel mix (~20 ul) is loaded on each glass slide inside the Teflon frame and covered with a teflonated cover. The cover is pressed against the frame's substrate to form a thin (50-100 µm thick) gel plate and locked.
4. The slides are placed horizontally into the argon chamber, which is then filled with argon). The gels polymerize for ~30 minutes.
5. The slides are removed from argon chamber, un-coverslipped, and the excess Acrylamide monomer is washed off with DI H2O for 30 min.

B. PCR Reactions

Performing PCR on the above constructed slides is conducted according to the following general protocol:

6. Prepare diffuse-in mix (200 uL total volume): [152.33 uL dH2O, 10 uL 5 mM unlabeled dNTP mix (Gibco-BRL), 20 uL 10× Taq Buffer (with MgCl2) (Sigma-Aldrich), 1.33 uL 30% BSA, 2 uL 10% Tween-20 (Sigma-Aldrich), 1 uL unmodified amplification primer B (100 uM), 13.33 uL Jumpstart TAQ (2.5 units/uL) (Sigma-Aldrich), and 0.5 uL Template (~10 fM)]. For negative controls, gel slides are prepared that lack: template, or amplification primer(s), or TAQ polymerase.
7. The slides are placed face up in PCR hood and PCR reagents are diffused in: 25 uL of diffuse-in mix is Pipetted to the center of each gel, and teflonated cover slides are applied to spread the liquid evenly over the surface of the gel. (This protocol is compared with its modification, which includes all PCR reagents in the gel mix before casting, and PCR efficiencies are compared and suitability for use in the invention is determined as appropriate.)
8. Lock down the edges of the coverslipped slides with plastic clips. If necessary, the slides may be covered with mineral oil to prevent evaporation, e.g., in a SecureSeal (Grace Biolabs) chamber.
9. Slides are placed in Thermal Cycler (PTC-0200, MJ Research) and undergo PCR cycling as follows: 3 minutes at 94° C., 40 to 45 cycles of (94° C.×45 seconds, 58° C.×30 seconds, and 72° C.×3 minutes), followed by 72° C.×6 minutes, and then slides can be cooled to 4° C. for storage. Both the annealing temperature, and the extension time are adjusted to optimize for our set of amplification primers and for longer templates, respectively.
10. Slides are removed from thermal cycler, coverslips are removed from slides, and gels are washed 2 times by 4 minutes with washing buffer [10 mM Tris-HCl, pH 7.5, 50 mM KCl, 2 mM EDTA, 0.01% Triton X-100], in which they may be stored.
11. The slides are assessed for the growth of DNA clones. One procedure involves visualizing the polonies by staining the gels for 20 min with SYBR Green I (in diluted 5000-10000 fold in 50 mL 0.5× TBE), washing with 0.5× TBE, and then imaging the gels on a slide scanner (e.g., ScanArray LITE Micro array Analysis System, Packard) or under fluorescent scanning confocal microscope (LSM 510/ConfoCor 2 combi, Zeiss, or Scanarray 5000, Perkin-Elmer). Plates are marked underneath to indicate some polonies for further manipulations. Colonies are assessed by their size and brightness. Another procedure consists of excising labeled polonies from gel, followed by eluting the PCR product from the gel pellets and purifying it on Qiaquick columns (Qiagen), and assessing the amplified template by electrophoretic fragment analysis and sequencing.

Alternative gel casting procedures can be performed to determine a final optimization for some embodiments contemplated by the present invention. For example, one alternative procedure tests different gel chemistries for the highest PCR output. For example, we use a gel mix without toxic and potentially DNAreactive TEMED and APS. In this case, the gel is cured with UV light (Rubina et al., 2004). In addition, methacrylamide modified oligonucleotides have been reported to have a high degree of immobilization. (Rubina et al., 2004).

In another alternative procedure, the suitability of longer linkers between methacrylamide groups and oligonucleotides is assessed. The objective of this procedure is to test primers in reduced concentrations (down to 0.2 uM) in order to exhaust them in the amplification process, yet not to limit amplification.

In another alternative procedure, an exact gel concentration can be determined for various template sizes to control polony growth within a 30-50 um diameter.

C. Spotting of DNA Templates

When optimal gel and PCR chemistries and parameters are established, procedures to optimize spotting templates on a gel surface can be performed.

These experiments are conducted first with a picoliter injector (Stoelting) driven by micromanipulator with cassettes placed on motorized XY precision stage. Gels are prepared as above (i.e., A; Steps 1-5), wherein a new Step 6 comprises spotting a 100 pL of diffuse-in mix on a gel surface. This protocol establishes an empirical determination of the spotting procedure, its parameters and chemistries. Inherent in this procedure is to exclude DNA absorption by the walls of template container (Blanchard et al., 1996).

After this procedure is established, template spotting using an ink-jet printer head concept is laid out. (Blanchard et al., 1996; Hughes et al., 2001). After spotting, gel frames are covered with teflonated slides and locked. Then they are thermocycled and treated as in steps 9 through 11. Templates of different length are spotted along with additional different (or all) components of PCR mix. The spotted gels are assessed as in (B) above. Assessments include the possibility that DNA molecules float far sideways from a deposition spot, which would affect the precision of addressing. As one precaution, gels are unsaturated with solutions, so that a drop of diffuse-in solution is not floating but absorbed by the gel.

D. Cycle Sequencing

After a reliable and reproducible polony growth is achieved, a protocol is developed for conducting cycle-sequencing reaction on gel-immobilized strands of extended A-primers.

After polony amplification and washout, the immobilized dsDNA is denatured and the unattached DNA strand is removed by incubating the plate in 70° C. denaturing buffer (70% formamide) for 15 min and performing electrophoresis in 0.5× TBE (90 mM Tris/64.6 mM boric acid/2.5 mM EDTA, pH 8) with 42% urea for 1 h at 5-10 v/cm. Then the slides are washed 2×4 min in wash buffer (10 mM Tris-HCl, pH 7.5, 50 mM KCl, 2 mM EDTA, 0.01% Triton X-100). An annealing mix (0.25-1 uM sequencing primer, 0.15 M NaCl/10 mM phosphate, pH 7.4/1 mM EDTA/0.01% Triton X-100) is added over the gel. To hybridize the immobilized A-primed ssDNA to the sequencing primer (free reverse universal primer B), the slides are heated at 94° C. for 2 min, then at 56° C. for 15 min. Unannealed excess primer is removed by immediately washing the slides 2×4 min in wash buffer. The slides are then washed in DI H2O 3×5 min, and the excess water is removed/dried.

The sequencing reaction mix (20 µL of Big Dye Terminator Sequencing Mix (Applied Biosystems) and 20 µL of PCR-grade water) is poured over the slide. Sequencing extension fragments are generated in 10-25 cycles according to ABI specifications (e.g., denaturation at 96° C. for 10 s, primer annealing at 50° C. for 10 s, extension at 60° C. for 4 min, and a final 4° C. hold). The slides are then washed in DI H2O 3×5 min, and the excess water is removed/dried. The protocol is optimized by repeating it with decreasing amounts of Big Dye Terminator reagent.

Initial experiments using an SB sequencer demonstrated that sufficient signal may be obtained with 1/500th of Big Dye Standard. Consequently, the amount of Big Dye reagent is decreased until an optimum amount of sequencing reagent necessary for reliable detection is determined. Also, the primary reactions are optimized by varying the amounts of buffer components, primers, reaction volumes and cycling times.

E. Primer Washout

It is believed that very little (or none) sample clean-up is needed because gel-bound primers ensure that their ddNTP-terminated extension products are also bound and can not undergo electrokinetic injection and electrophoresis. In addition, primer availability may be limited by reducing their concentration, e.g., 3-fold, and thus exhausting them by the end of PCR (Mitra et al., 2003).

F. Isothermal Sequencing Reactions

The sequencing technology contemplated by the present invention is compatible with the use of isothermal reactions. One of the major technical advances in automated sequencing has been the implementation of cycle sequencing. This application of Sanger-based sequencing has led to the robust processing that has made large-scale sequencing possible. However, it is not without drawbacks.

In terms of cost, cycle sequencing usually requires the use of expensive thermolabile polymerases, instead of the cheaper, and more readily available thermostable polymerases. Additionally, enzyme processivity (especially in homopolymeric regions) have distinct advantages when used in isothermal reactions as compared to cycle sequencing. For example, in some types of reactions, even 3 cycles of isothermal extension (versus 25-30 cycles in cycle sequencing) made a dramatic impact on sequence quality. The testing is performed as described above, with standard templates in a systematic fashion. If the reactions on standard templates are successful, testing the reactions on a range of problematic templates is also be performed.

G. Linear MMCA-Mediated Electrophoresis

Slides are prepared in accordance with (B) and (C), above, and covered with 40 µL of HiDi Formamide (Applied Biosystems), incubated at 95° C. for 2 min, and snap-cooled to 4° C. in a CoolSafe® block (Diversified Biotech), then warmed to room temperature. Single CE capillary and linear MMCA are attached to the gel surface at the earlier marked site of a polony. Extension fragments are injected in the capillary by passing a current between flat electrode and capillaries. Then electrophoretic separation is run Experiments are repeated to study and characterize the diffusion of denatured fragments within the gel, as well as to prevent fragments from one spot to contaminate a neighboring spot. The electrokinesis of ssDNA fragments (obtained from Big Die Standard kit or generated in gel during Sanger reaction) on the gel when current is applied between a single capillary above and a flat electrode beneath several neighboring polonies are also be characterized. Further study, characterization, and optimization of the electrophoresis of ssDNA fragments using first a single capillary and then a linear MMCA are compared. The need for a separate step for electrokinetic injection of a sample plug is thoroughly investigated because extension products in this thin gel plate may behave as a sample plug. Parameters of injection and run, separation times and length with different media, and fluorescent signal amplitude are thoroughly investigated also.

H. Signal Optimization

The goal of these experiments is to achieve the highest signal with the simplest procedure. Data on the need and degree of washout steps may allow streamlining the entire protocol in order to attain the highest signal with no or minimal sample clean-up.

I. Washing and Storing Optimization

The goal of these experiments is to achieve optimization of procedures for washing and storing of the gel cassettes with clones, as well as re-amplification and re-sequencing of the stored clones.

J. Electrophoresis and Detection Using a 3,000-Lane 2D-MMCA

Using an automated DNA sequencer comprising reusable gel plate cassettes and addressed wiring, gel-based amplification and sequencing are performed using a 64×48 2D MMCA. Studies are performed to optimize the array attachment to the gel surface, injection and run parameters, and fluorescence detection. Finally, a 2D MMCA electrophoresis protocol is developed to enable sequencing at 1,000 bp/second with a 400 base pair Q20 read length at cost of $0.005/kbp.

Example 4

A 2D-MMCA Prototype Comparison with an ABI Sequencer

This example describes a comparative experiment to assess a 2D-MMCA prototype against an ABI-3700 sequencer using a range of templates.

1. The instrument is initially compared using a pCR2-1-TABS3-D5 template and pGEM vector controls. The templates are amplified and sequenced on gels at varying reaction conditions. The results of these reactions are compared to the known sequence of the template.

2. Randomly selected clones from the CSHL Genome Center are selected for sequencing comparisons. These clones are sequenced at varying reaction conditions and the results compared to the same templates sequenced in parallel on the ABI-3700.

3. A sequencing project using a 48×64-capillary array utilizes clones from an already sequenced BAC and re-sequence them on the prototype sequencer. The sequence of an 8× assembly done this way is compared to the finished sequence as determined by an ABI-3700. This comparison is repeated for 3-5 additional BACs not only to determine the accuracy of the prototype sequencer but also to determine the amount of finishing typically required after using this sequencing in comparison to the ABI-3700.

Example 5

De Novo Sequencing: 3-5 Kilobase DNA Read Pairs

This example describes the development of technology for growing twin clones and obtaining readpairs of 3-5 kbp DNA templates as an approach to de-novo sequencing.

1. Design and Fabrication of Mirror-Symmetrical Pairs of Reusable Gel Plate Cassettes.

Based on a developed design, reusable gel plate cassettes are designed and fabricated that are mirror-symmetrical pairs of each other. For each set of DNA colonies, the paired plates can face-to-face cover and seal each other. They are used for growing individual PCR clones into two face-to-face adjacent gel layers that form when the paired cassette is closed during thermocycling. As a result, upon opening/separation of the gels, twin polonies are formed, each plate containing one of the twin clones. The paired cassettes enable the generation of sense and antisense sequencing of the twin clones and obtain read pairs for long templates, which is critical for de novo sequencing. In particular, some cassettes incorporate 5×7 mm electrodes while some cassettes have larger electrodes for 96×316 lane MMCAs (exact dimensions are established empirically). The plates also have reference points for addressed spotting and reading.

2. PCR Cloning of 3-5-10 Kbp Long DNA

PCR and sequencing protocols are further optimized to achieve PCR cloning with efficient amplification and cycle sequencing of 3-5 kbp up to 10 kbp DNA fragments. Based on reported results, the main factor is the density of the gel. (Mita & Church, 1999). Longer templates are cloned in gels with lowered acrylamide concentration.

3. Growing Twin Clones

Developing an optimized technique involves enabling growth of individual PCR clones into two face-to-face adjacent gel plates in paired cassettes. A simple procedure resulting in twin polonies upon separation of the gels is optimal. Furthermore, twin clones may have different sets of primers in order to allow sense and antisense sequencing of the twin clones on adjacent mirror-paired gel plates.

a. The PCR gel mix preparation and casting are done as described above with the following modifications: two sets of the mix are prepared; mix A containing from 0.2 up to 1 µM of primer A with acrydite modification at its 5' end and 0.2 up to 1 µM of free primer B is prepared for the plate A. Similar mix (mix B) is prepared for the plate B, only with acrydite-modified primer B and free primer A.

b. The PCR mix A is poured onto plate A, and mix B fills plate B. They are covered with teflonated glass or plastic coverslip and polymerized. As a result, plate A of each pair contains primers A covalently bound to the gel and free primers B, and plate B contains primer B bound to the gel and free primer A. The frames with gel-plates are washed, sealed and stored at 4° C.

c. The template solution is dispensed in 0.1 nl portions using a special high precision printer head or spotting machine and 2D-positioning stage for precise spotting of the solution on gel plates. The droplets (~Ø30 µm) of the template solution are spotted only on one gel of a pair, say the gel plate A, with 100 µm pitch. The spots are organized in clusters, 48×64 spots each, 8×12 such clusters in a plate, for a total of 294,912 spots in 96 zones on the gel. In gel cassettes for 96×316 lane MMCAs, there are 30,336 spots in each clusters for a total of 2912256 spots on the gel plate. Due to Poisson distribution, about 36% of the spots are empty, ~36% of the spots contain single template molecules and thus produce single clone colonies, and remaining ~28% of the spots contain two or more template molecules and generate mixtures of DNAs.

d. Plate B is turned over to cover and seal plate A: the two gels face and contact each other in a sandwich between two plate mounts. The gel sandwich is placed into a thermocycler and cycled 40 times. We plan to have polonies of 30-50 µm in diameter. Since polony size is inversely proportional to the template length and the gel density (Mita & Church, 1999), for a given template one adjusts the acrylamide concentration to keep the DNA colony within indicated dimensions.

e. After completion of the PCR cycling, the gel plate sandwich is open and the gels are separated. Each gel now contains DNA colonies that are mirror-image replicas of their twin colonies on paired gel. Plates undergo wash-out with denaturing step as described above. The difference is in that on plate A, A-primed single DNA strands are linked to the gel by their 5' ends, whereas on plate B complimentary B-primed single DNA strands are linked to the gel.

f. A sequencing reaction mix (Big Dye) is poured on the gel plates. Note that mix for plate A contains sequencing primer B, and mix for plate B contains sequencing primer A. The separated gel plates are covered with a teflonated cover slide and thermocycled 10-25 times. After the cycle sequencing is completed, the plates are opened, washed and a denaturing buffer is added. Plate A now contains free B-primed dye-terminated sense sequencing products and bound A-primed dye-terminated antisense sequencing products, as well as PCR products (bound A-primed antisense strands and free B-primed sense strands). Plate B contains free A-primed dye-terminated antisense sequencing products and bound B-primed dye-terminated sense sequencing products, as well as PCR products (bound B-primed sense strands and free A-primed antisense strands). As a result of the proposed configuration, both sense (plate A) and antisense (plate B) sequencing products are generated in direct sequencing of polonies without or with minimal polony clean-up. A polony tracking software allows linking the separate reads from plates A and B in read pairs for further use in the sequencing assembly. In order to reduce the role of free primers from contralateral gel, the sequencing primers are added in excess to win competition for polymerase (Hashimoto et al., 2003). If a diffusion of free primers from contralateral gel is too strong, it results in an error due to detectable reverse sequencing products.

In this case, the concentration of the free primers is reduced while adding a proportion of the same primers in acrydite-modified form with longer linkers. Thus, each gel plate contains immobilized forward primers and free and bound reverse primers. The ratio between the free and bound primers is established empirically so that the free primers are exhausted by the end of PCR. If the problem still remains, after the PCR a step of exonuclease degradation of the primers followed by heat inactivation of the enzyme is included. (Werle E et al., 1994).

Another approach: leave open a paired cassette during first few cycles of PCR, and then close it at later cycles. This works rather like a colony replication, which is another advantage of the polonies. This reduces time during which contralateral diffusion may occur. Earlier plate separation is also tried, because once a twin clone is seeded, it will grow on its own.

g. MMCA is attached to the gel surface and capillary electrophoresis is conducted as described above. An optimized protocol for sense and antisense sequencing of the twin clones on adjacent mirror-paired gel plates is developed. A production-scale growing and sequencing of twin clones in paired reusable gel plate cassettes is demonstrated. Electrophoretic detection of sense and antisense sequencing information and generation of forward and reverse read-pairs from the twin polonies using prototype instrument with 96×316 lane 2D-MMCA are obtained. Statistically significant data on the read length of sequenced twin polonies at Q20 depending on injection and running conditions are obtained. A 400-450 base pair read length at Q20 in 10-20 min, a 800 base pair read length at Q20 in 25-35 min, and a 65-90 min in IPN-60 and POP-7 media are obtained.

Example 6

Electrokinetic Injection from Micro-Gel Pads

This example demonstrates the visualization of electrokinetic injection flow.

A modified DNA sequencer configured with an electrokinetic injection system positioned a capillary over a gel pad slide such that there was overlap between an individual gel pad and a single capillary internal diameter. A buffer layer interface layer between the gel pad and the capillary acted as the transfer medium for the DNA product. See FIG. 21A-C.

The effective injection spot size is directly proportional (i.e., a positive correlation) to the interface distance between the capillary and the gel pad. See FIG. 22. Specifically, the effective spot size increases with the increase of the distance. For example, when using 50 mm ID capillary and 100 mm gel pads, the optimum distance for electrokinetic injection was empirically determined to be approximately 100 mm. This distance ensures injection from the entire gel pad.

Injection parameters and characteristics of the gel matrix were also optimized by testing electrokinetic injection from gel pads with various compositions of polymer and cross-linker. This experiment compared electrokinetic injection of different gel compositions followed by CE separation of the Internal Lane Standard (ILS, Promega) using BigDye-3.1 DNA sequencing Standard (ABI). The data show optimal gel compositions were a function of both cross-linker and gel monomer composition. See FIG. 23.

Electrokinetic injection of DNA samples into gel pads was performed according to the following protocol:

1. Incubated gel pad slide in boiling water (i.e., for example approximately 100° C.) for 10 minutes. Although it is not necessary to understand the mechanism of an invention, it is believed that this step opens the pores of dry gel pads.
2. Dehydrated the gel pad slide and placed a frame seal on the slide.
3. Added 10 µl of DNA sample, diluted and denatured in 20% formamide.
4. Infusion step: Covered the frame seal and heated the slide at 60° C. for 10 minutes.
5. Collected leftover material from the slide.
6. Washed the slide with distilled water
7. Added distilled water in the frame seal.
8/ Performed an electrokinetic injection of the sample from the gel pad into a capillary.

An optimum gel composition for capillary electrophoresis was chosen by determining the separation quality and the pattern of the respective peak heights. These data also show that the separation quality and peak pattern are very similar between a conventional sample loading injection and an electrokinetic sample loading injection. See FIG. 24A/B.

The data shows a satisfactory separation quality for DNA fragments shorter than 200 bp. For longer fragments a significant signal decrease was observed as compared to the control sample. See FIG. 28A/B. Although it is not necessary to understand the mechanism of an invention, it is believed that this decrease is related to retardation of longer fragments by the gel pad matrix. It is hypothesized that this effect may be minimized by using gel pads with a larger pore size.

REFERENCES

1. Abril et al., (2002). Initial sequencing and comparative analysis of the mouse genome. *Nature* 420, 520-562.
2. Alaverdian et al., (2002). A family of novel DNA sequencing instruments based on single-photon detection. *Electrophoresis* 23, 2804-2817.
3. Bilenko et al., (2003). Formation of a resistive region at the anode end in DNA capillary electrophoresis. *Electrophoresis* 24, 1176-1183.
4. Blanchard et al., (1996). High-density oligonucleotide arrays. *Biosensors and Bioelectronics* 11, 687-690.
5. Braslaysky et al., (2003). Sequence information can be obtained from single DNA molecules. *Proc. Natl. Acad. Sci.* 100, 3960-3964.
6. Brenner et al., (2000). Gene expression analysis by massively parallel signature sequencing (MPSS) on microbead arrays. *Nat. Biotechnol.* 18, 630-634.
7. Chetverina et al., (1993). Cloning of RNA molecules in vitro. *Nucleic Acids Res.* 21, 2349-2353.
8. Chetverina et al., (2002). Molecular colony diagnostics: detection and quantitation of viral nucleic acids by in-gel PCR. *Biotechniques* 33, 150-2, 154, 156.
9. Deamer et al., (2000). Nanopores and nucleic acids: prospects for ultrarapid sequencing. *Trends in Biotechnology* 18, 147-151.
10. Dressman et al., (2003). Transforming single DNA molecules into fluorescent magnetic particles for detection and enumeration of genetic variations. *Pro. Natl. Acad. Sci.* 100, 8817-8822.
11. Drmanac et al., (1998). Accurate sequencing by hybridization for DNA diagnostics and individual genomics. *Nature Biotechnol.* 16, 54-58.
12. Emrich et al., (2002). Microfabricated 384-lane capillary array electrophoresis bioanalyzer for ultrahigh-throughput genetic analysis. *Anal. Chem.* 74, 5076-5083.
13. Gavrilov et al., (2003). Dynamic range of fluorescence detection and base-calling accuracy in DNA sequencer based on single-photon counting. *Electrophoresis* 24, 1184-1192.
14. Gillespi et al., (1965). A Quantitative Assay for Dna-Rna Hybrids with Dna Immobilized on A Membrane. *J. Mol. Biol.* 12, 829-&.

15. Gorfinkel et al., Multicapillary bundle for electrophoresis and detection for DNA. U.S. Pat. No. 6,464,852 (2002). Filed: Dec. 11, 1999.
16. Hashimoto et al., (2003). On-line integration of PCR and cycle sequencing in capillaries: from human genomic DNA directly to called bases. *Nucleic Acids Research* 31, e41.
17. Heller, C. (2000). Influence of electric field strength and capillary dimensions on the separation of DNA. *Electrophoresis* 21, 593-602.
18. Hughes et al., (2001). Expression profiling using microarrays fabricated by an ink-jet oligonucleotide synthesizer. *Nat. Biotechnol.* 19, 342-347.
19. Kafatos et al., (1981). Dot hybridization and hybrid-selected translation: methods for determining nucleic acid concentrations and sequence homologies. *Gene Amplif. Anal* 2, 537-550.
20. Kartalov et al., (2004). Microfluidic device reads up to four consecutive base pairs in DNA sequencing-by-synthesis. *Nucleic Acids Research* 32, 2873-2879.
21. Khrapko et al., (1989). An oligonucleotide hybridization approach to DNA sequencing. *FEBS Lett.* 256, 118-122.
22. Korlach et al., (2001). A new strategy for sequencing individual molecules of DNA. *Biophysical Journal* 80, 147A.
23. Koutny et al., (2000). Eight hundred base sequencing in a microfabricated electrophoretic device. *Analytical Chemistry* 72, 3388-3391.
24. Lage et al., (2003). Whole genome analysis of genetic alterations in small DNA samples using hyperbranched strand displacement amplification and array-CGH. *Genome Research* 13, 294-307.
25. Leamon et al., (2003). A massively parallel PicoTiterPlate based platform for discrete picoliterscale polymerase chain reactions. *Electrophoresis* 24, 3769-3777.
26. Levene et al., (2003). Zero-mode waveguides for single-molecule analysis at high concentrations. *Science* 299, 682-686.
27. Lipshutz et al., (1995). Using Oligonucleotide Probe Arrays to Access Genetic Diversity. *Biotechniques* 19, 442-447.
28. Lizardi et al., (1998). Mutation detection and single-molecule counting using isothermal rolling-circle amplification. *Nat. Genet.* 19, 225-232.
29. Margraf et al., (2004). Single-Tube Method for Nucleic Acid Extraction, Amplification, Purification, and Sequencing. *Clinical Chemistry* 50, 1755-1761.
30. Maskos et al., (1993). A Novel Method for the Analysis of Multiple Sequence Variants by Hybridization to Oligonucleotides. *Nucleic Acids Research* 21, 2267-2268.
31. Meller et al., (2000). Rapid nanopore discrimination between single polynucleotide molecules. *Proc. Natl. Acad. Sci. U.S.A* 97, 1079-1084.
32. Mitra et al., (1999). In situ localized amplification and contact replication of many individual DNA molecules. *Nucleic Acids Res.* 27, e34.
33. Mitra et al., (2003). Fluorescent in situ sequencing on polymerase colonies. *Anal. Biochem.* 320, 55-65.
34. Nagai et al., (2001). Development of a microchamber array for picoliter PCR. *Anal Chem* 73, 1043-1047.
35. Paegel et al., (2003). Microfluidic devices for DNA sequencing: sample preparation and electrophoretic analysis. *Current Opinion in Biotechnology* 14, 42-50.
36. Pati et al., (2001), Blocks of limited haplotype diversity revealed by high-resolution scanning of human chromosome 21. *Science* 294, 1719-1723.
37. Pourmand et al., (2002). Multiplex Pyrosequencing. *Nucleic Acids Research* 30, e31.
38. Ronaghi et al., (1996). Real-time DNA sequencing using detection of pyrophosphate release. *Anal. Biochem.* 242, 84-89.
39. Ronaghi, M. (2001). Pyrosequencing Sheds Light on DNA Sequencing. *Genome Research* 11, 3-11.
40. Rubina et al., (2004). Hydrogel drop microchips with immobilized DNA: properties and methods for large-scale production. *Analytical Biochemistry* 325, 92-106.
41. Sanger et al., (1977). DNA sequencing with chain-terminating inhibitors. *Proc. Natl. Acad. Sci. U.S.A* 74, 5463-5467.
42. Shendure et al., (2004). Advanced sequencing technologies: methods and goals. *Nat. Rev. Genet.* 5, 335-344.
43. Singer et al., (1997). Libraries for genomic SELEX. *Nucleic Acids Res* 25, 781-786.
44. Soper et al., (1998). Sanger DNA-sequencing reactions performed in a solid-phase nanoreactor directly coupled to capillary gel electrophoresis. *Anal Chem.* 70, 4036-4043.
45. Southern et al., (1999). Molecular interactions on microarrays. *Nat. Genet.* 21, 5-9.
46. Strizhkov et al., (2000). PCR amplification on a microarray of gel-immobilized oligonucleotides: Detection of bacterial toxin- and drug-resistant genes and their mutations. *Biotechniques* 29, 844-857.
47. Tillib et al., (2001). Advances in the analysis of DNA sequence variations using oligonucleotide microchip technology. *Current Opinion in Biotechnology* 12, 53-58.
48. Tillib et al., (2001). Integration of Multiple PCR Amplifications and DNA Mutation Analyses by Using Oligonucleotide Microchip. *Analytical Biochemistry* 292, 155-160.
49. van den Boom et al., (1998). Forward and Reverse DNA Sequencing in a Single Reaction. *Analytical Biochemistry* 256, 127-129.
50. Vasiliskov et al., (1999). Fabrication of microarray of gel-immobilized compounds on a chip by copolymerization. *Biotechniques* 27, 592-8, 600.
51. Walker et al., (1992). Isothermal in vitro amplification of DNA by a restriction enzyme/DNA polymerase system. *Proc. Natl. Acad. Sci. U.S.A* 89, 392-396.
52. Westin et al., (2000). Anchored multiplex amplification on a microelectronic chip array. *Nat. Biotechnol.* 18, 199-204.
53. Winters-Hilt et al., (2003). Highly accurate classification of Watson-Crick basepairs on termini of single DNA molecules. *Biophys. J.* 84, 967-976.
54. Gorfinkel et al., (1998) Method and apparatus for identifying fluorophores. U.S. Pat. No. 5,784,157. Filed: Nov. 21, 1995.

We claim:
1. A system for nucleic acid analysis comprising
  a) a plurality of pads disposed on a solid substrate, at least a portion of said pads comprising nucleic acid, at least a portion of said nucleic acid comprising a marker, said substrate comprising an electrically conductive element;
  b) a plurality of capillaries, each said capillary comprising first and second ends, said first end alignable with a pad in said plurality of pads without contacting said pad, said second end alignable with
  c) a photodetector configured to detect said marker when said nucleic acid is in said capillaries.
2. The system of claim 1, further comprising
  d) a buffer reservoir, wherein each said capillary is in fluid communication with said reservoir;

e) a means of electrically biasing at least a portion of said plurality of capillaries with respect to said electrically conductive element such that an electric current passes through said pad and said capillary to said reservoir, f) an illumination source capable of side-illuminating at least a portion of said plurality of capillaries near said second end of each capillary in said portion such that said marker emits a photon detectable by said photodetector, and g) a means for processing data acquired by said plurality of photodetectors.

3. A method of nucleic acid analysis, comprising a) providing the system of claim 2;

b) aligning said plurality of capillaries with said plurality of pads without contacting said pads with said capillaries; and c) causing an electric current to pass through at least a portion of said pads and at least a portion of said capillaries to said reservoir by said means of electrically biasing at least a portion of said plurality of capillaries with respect to said electrically conductive element such that at least a portion of said nucleic acid enters said first ends of at least a portion of said capillaries.

4. The method of claim 3, further comprising:

d) aligning said plurality of photodetectors with said second ends of said plurality of capillaries; and e) detecting nucleic acid in at least a portion of said capillaries by detecting said marker.

5. The method of claim 4, wherein said marker emits a photon upon excitation with said illumination source.

6. The method of claim 5, wherein said marker is selected from the group consisting of dyes and fluorophores.

7. The system of claim 1 wherein said photodetector faces said second end of said capillary.

8. The system of claim 7 wherein said buffer reservoir is transparent and is interposed between said photodetector and said capillary.

9. The system of claim 8 further comprising a diffusion barrier surrounding each said pad.

10. The system of claim 9 comprising a removable dam that is capable of retaining liquid on a specified region of said pad array.

11. The system of claim 10 comprising a dam top cover.

12. The system of claim 1 wherein said plurality of pads is configured as a two-dimensional array.

13. The system of claim 12 further comprising a spotting machine, wherein said spotting machine is capable of spotting said array of pads in register with said capillary array.

14. The system of claim 1 wherein said plurality of capillaries is cross-sectionally a two-dimensional array.

15. The system of claim 14 wherein said plurality of capillaries is a monolith.

16. The system of claim 1 wherein said electrically conductive element is discontinuous such that each said pad is electrically isolated from all other said pads.

17. The system of claim 16 wherein at least one said pad is in electrical contact with at least one other said pad.

18. The system of claim 1 wherein said illumination source is a laser configured to emit a beam capable of entering said capillary array normal to a sidewall of said capillary array and exiting said capillary array normal to a wall opposite said sidewall.

19. The system of claim 18 wherein said laser beam scans said capillary array.

20. The system of claim 18 wherein said laser beam traverses an optical line generator before entering said capillary array.

21. The system of claim 18 wherein said laser beam comprises mutually focused, temporally modulated beams.

22. The system of claim 1 wherein said photodetector is a single photon detector.

23. The system of claim 22 wherein said laser beam excites an emission of light from a fluorophore traversing said capillary, said emission collected as said emission exits said first end of said capillary.

24. The system of claim 23 wherein a fiber optic device collects said emission.

25. The system of claim 24 wherein said fiber optic device and said laser beam scan said monolith in synchrony.

26. The system of claim 1 wherein said capillary array is more than about 8 capillaries to less than about 400 capillaries in a first direction and more than about 8 capillaries to less than about 400 capillaries in a second direction orthogonal to said first direction.

27. The system of claim 26 wherein said capillary array is more than about 700 capillaries.

28. The system of claim 1 wherein said capillary has a thickness of more than about 30 micrometers and less than about 100 micrometers.

29. The system of claim 28 wherein said capillary has a bore of more than about 900 square micrometers and less than about 2500 square micrometers.

30. The system of claim 29 wherein said capillary comprises fused silica.

31. The system of claim 1 wherein said pad has a water holding capacity of more than about 100 picoliters.

32. The system of claim 1 wherein said capillary has a length of more than about 5 cm and less than about 20 cm.

33. The system of claim 1 wherein an array of said photodetectors is capable of detecting colors.

* * * * *